(12) United States Patent
Fahmy et al.

(10) Patent No.: US 8,629,098 B2
(45) Date of Patent: Jan. 14, 2014

(54) COMPOSITIONS AND METHODS FOR ADOPTIVE AND ACTIVE IMMUNOTHERAPY

(75) Inventors: Tarek Fahmy, New Haven, CT (US); Erin Steenblock, Janesville, WI (US)

(73) Assignee: Yale University, New Haven, CT (US)

( * ) Notice: Subject to any disclaimer, the term of this patent is extended or adjusted under 35 U.S.C. 154(b) by 468 days.

(21) Appl. No.: 12/812,304

(22) PCT Filed: Jan. 14, 2009

(86) PCT No.: PCT/US2009/030966
§ 371 (c)(1),
(2), (4) Date: Jul. 9, 2010

(87) PCT Pub. No.: WO2009/094273
PCT Pub. Date: Jul. 30, 2009

(65) Prior Publication Data
US 2010/0284965 A1 Nov. 11, 2010

Related U.S. Application Data

(60) Provisional application No. 61/021,258, filed on Jan. 15, 2008.

(51) Int. Cl.
*C07K 14/00* (2006.01)
*A61K 38/00* (2006.01)

(52) U.S. Cl.
USPC .............................................. 514/2; 424/85.1

(58) Field of Classification Search
None
See application file for complete search history.

(56) References Cited

U.S. PATENT DOCUMENTS

| | | |
|---|---|---|
| 3,960,757 A | 6/1976 | Morishita |
| 6,620,617 B2 | 9/2003 | Mathiowitz |

FOREIGN PATENT DOCUMENTS

| | | |
|---|---|---|
| WO | 9321906 | 11/1993 |

OTHER PUBLICATIONS

Abken, et al., "Tuning tumor-specific T-cell activation: a matter of costimulation", Trends Immunol., 23:240-245 (2002).
Aguado and Lambert, "Controlled-release vaccines—biodegradable polylactide/polyglycolide (PL/PG) microspheres as antigen vehicles", Immunobiology, 184(2-3):113-25 (1992).
Anderson and Shive, "Biodegradation and biocompatibility of PLA and PLGA microspheres", Adv. Drug Deliv. Rev., 28:5-24 (1997).
Auffray, et al., "Isotypic and allotypic variation of human class II histocompatibility antigen alpha-chain genes", Nature, 308(5957):327-333 (1984).
Beck, et al., "A new long-acting injectable microcapsule system for the administration of progesterone", Fertil. Steril., 31:545 (1979).
Beck at al., "New long-acting injectable microcapsule contraceptive system", Am. J. Obstet. Gynecol., 135(3):419-426 (1979).
Benita, at al., "Characterization of drug-loaded poly(d,l-lactide) microspheres", J. Pharm. Sci., 73:1721 (1984).
Bergmann, et al., "An endogenously synthesized decamer peptide efficiently primes cytotoxic T cells specific for the HIV-1 envelope glycoprotein", Eur. J. Immunol., 23:2777-2781 (1993).
Bergmann, et al., "Flanking residues alter antigenicity and immunogenicity of multi-unit CTL epitopes", J. Immunol., 157:3242-3249 (1996).
Braciale, "Antigen processing for presentation by MHC class I molecules", Curr. Opin. Immunol., 4:59-62 (1992).
Bramwell, et al., "Particulate delivery systems for biodefense subunit vaccines", Adv. Drug Deliv. Rev., 57(9):1247-65 (2005).
Burke, et al., "The influence of adjuvant on the therapeutic efficacy of a recombinant genital herpes vaccine", J. Inf. Dis. 170:1110-19 (1994).
Chambers and Allison, "Co-stimulation in T cell responses", Curr. Opin. Immunol., 9:396-404 (1997).
Cohen, et al., "Controlled delivery systems for proteins based on poly(lactic/glycolic acid) microspheres", Pharmaceutical Res., 8:713-20 (1991).
Curtsinger, et al., "Signal 3 determines tolerance versus full activation of naice CD8 T cells: dissociating proliferation and development of effector function", J. Exper. Med., 197:1141-1151 (2003).
Deeths and Mescher, "B7-1-dependent co-stimulation results in qualitatively and quantitatively different responses by CD4+ and CD8+ T cells", Eur. J. Immunol., 27:598-608 (1997).
Dudley and Rosenberg, "Adoptive-cell-transfer therapy for the treatment of patients with cancer", Nat. Rev. Cancer, 3:666-675 (2003).
Fahmy, et al., "Increased TCR avidity after T cell activation: a mechanism for sensing low-density antigen", Immunity., 14:135-143 (2001).
Fahmy, et al., "Surface modification of biodegradable polyesters with fatty acid conjugates for improved drug targeting", Biomaterials, 26: 5727-5736 (2005).
Fyfe, et al., "Results of treatment of 255 patients with metastatic renal cell carcinoma who received high-dose recombinant interleukin-2 therapy", J. Clim. Oncol., 13:688-696 (1992).
Garlie, et al., "T cells coactivated with immobilized anti-CD3 and anti-CD28 as potential immunotherapy for cancer", J. Immunother., 22:336-45 (1999).

(Continued)

*Primary Examiner* — Anand Desai
(74) *Attorney, Agent, or Firm* — Pabst Patent Group LLP

(57) ABSTRACT

Modular aAPCs and methods of their manufacture and use are provided. The modular aAPCs are constructed from polymeric microparticles. The aAPCs include encapsulated cytokines and coupling agents which modularly couple functional elements including T cell receptor activators, co-stimulatory molecules and adhesion molecules to the particle. The ability of these aAPCs to release cytokines in a controlled manner, coupled with their modular nature and ease of ligand attachment, results in an ideal, tunable APC capable of stimulating and expanding primary T cells.

26 Claims, 11 Drawing Sheets

(56) References Cited

OTHER PUBLICATIONS

Gattinoni, et al., "Acquisition of full effector function in vitro paradoxically impairs the in vivo antitumor efficacy of adoptively transferred CD8+ T cells", Jour. Clin. Invest., 115:1616-26 (2005).
Guatelli et al., "Isothermal, in vitro amplification of nucleic acids by a multienzyme reaction modeled after retroviral replication", PNAS, 87:1874-1878 (1990).
Gupta, et al., "Poly(lactide-co-glycolide) microparticles for the development of single-dose controlled-release vaccines", Adv. Drug Deliv. Rev., 32(3):225-246 (1998).
Hentikoff and Hentikoff, "Amino acid substitution matrices from protein blocks",Proc. Natl. Acad. Sci. U.S.A., 89:10915-10919 (1992).
Hirano, et al., "Efficient presentation of naturally processed HLA class I peptides by artificial antigen-presenting cells for the generation of effective antitumor responses", Clin. Cancer Res., 12:2967-75 (2006).
Hogquist, et al., "T cell receptor antagonist peptides induce positive selection", Cell, 76:17-27 (1994).
Hori, et al., "Control of autoimmunity by naturally arising regulatory CD4+ T cells", Adv. Immunol, 81:331-371 (2003).
Itoh, et al., "Thymus and autoimmunity: production of CD25+CD4+ naturally anergic and suppressive T cells as a key function of the thymus in maintaining immunologic self-tolerance", J. Immunol., 162:5317-5326 (1999).
Jackson, et al., "Empty and peptide-containing conformers of class I major histocompatibility complex molecules expressed in *Drosophila melanogaster* cells", PNAS, 12117-12121 (1992).
Jain, "The manufacturing techniques of various drug loaded biodegradable poly (lactide-co-glycolide) (PLGA) devices", Biomaterials, 21:2475-2490 (2000).
Jaraswekin, et al., "Effect of poly(lactide-co-glycolide) molecular weight on the release of dexamethasone sodium phosphate from microparticles", J. Microencapsul, 24:117-128 (2007).
Jiang, et al., "Biodegradable poly(lactic-co-glycolic acid) microparticles for injectable delivery of vaccine antigens", Adv. Drug Deliv. Rev., 57(3):391-410 (2005).
Karim, et al., "Alloantigen-induced CD25+CD4 regulatory T cells can develop in vivo from CD25-CD4+ precursors in a thymus-independent process", J. Immunol, 172:923-928 (2004).
Kim, et al., "The ABC\s of artificial antigen presentation", Nat. Biotechnol, 22:403-10 (2004).
Kisielow, et al., "Tolerance in T-cell-receptor transgenic mice involves deletion of nonmature CD4+8+ thymocytes", Nature, 333:742-746 (1988).
Kohn, et al., "Single-step immunization using a controlled release, biodegradable polymer with sustained adjuvant activity", J. Immunol. Methods, 95 (1):31-8 (1986).
Kostelny, et al., "Formation of a bispecific antibody by the use of leucine zippers", J. Immunol., 148, 1547-1553 (1992).
Langer, et al., "New advances in microsphere-based single-dose vaccines", Adv. Drug Deliv. Rev., 28(1):97-119 (1997).
Langer and Folkman, "Polymers for the sustained release of proteins and other macromolecules", Nature, 263:797-780 (1976).
Latouche and Sadelain, "Induction of human cytotoxic T lymphocytes by artificial antigen-presenting cells", Nat. Biotechnol, 18:405-09 (2000).
Lehner, et al., "Antigen presentation: coming out gracefully", Curr. Biol., 8:R605-8 (1998).
Lenshow, et al., "CD28/B7 system of T cell costimulation", Annu. Rev. Immunol., 14:233-258 (1996).
Levine, et al., "Adoptive transfer of costimulated CD4+ T cells induces expansion of peripheral T cells and decreased CCR5 expression in HIV inflection", Nat. Med., 8:47-53 (2002).
Levine, et al., "Antiviral effect and ex vivo CD4+ T cell proliferation in HIV-positive patients as a result of CD28 costimulation", Science, 272:1939-43 (1996).

MacGlashan, et al., "Test of a theory relating to the cross-linking of IgE antibody on the surface of human basophils", J. Immunol., 135:4129-34 (185).
Manus, et al., "Ex vivo expansion of polyclonal and antigen-specific cytotoxic T lymphocytes by artificial APCs expressing ligands for the T-cell receptor, CD28 and 4-1BB", Nat. Biotechnol., 20:143-48 (2002).
Manus, et al., "HLA tetramer-based artificial antigen-presenting cells for stimulation of CD4+ T cells", Clin. Immunol., 106:16-22 (2003).
Mathiowitz, et al., "Morphology of polyanhydride microsphere delivery systems", J. Scanning Microscopy, 4:329-40 (1990).
Mathiowitz, et al., "Novel microcapsules for delivery systems", Reactive Polymers, 6:275-83 (1987).
Mescher, "Surface contact requirements for activation of cytotoxic T lymphocytes", J. Immunol., 149(7):2402-5 (1992).
Michel, et al., "CD28 as a molecular amplifier extending TCR ligation and signaling capabilities", Immunity, 15:935-945 (2001).
Miller and Heath, "Self-ignorance in the peripheral T-cell pool", Immunol. Rev., 133:131-150 (1993).
Mitchell, et al., "Phase I trial of adoptive immunotherapy with cytolyic T lymphocytes immunized against a tyrosinase epitope", J. Clin. Oncol., 20:1075-1086 (2002).
Needleman and Wunsch, "A general method applicable to the search for similarities in the amino acid sequence of two proteins", J. Mol. Biol., 48:443-453 (1970).
Oeike, et al., "Ex vivo induction and expansion of antigen-specific cytotoxic T cells by HLA-Ig-coated artificial antigen-presenting cells", Nat. Med., 9:619-24 (2003).
Papadopoulos, et al., "Infusions of donor leukocytes to treat Epstein-Barr virus-associated lymphoproliferative disorders after allogeneic bone marrow transplantation", N. Engl. J Med, 330:1185-91 (1994).
Pardoll, "Spinning molecular immunology into successful immunotherapy", Nat. Rev. Immunol., 2(4):227-38 (2002).
Prakken, et al., "Artificial antigen-presenting cells as a tool to exploit the immune" synapse\, Nat. Med., 6:1406-1410 (200).
Rathmell and Thompson, "The central effectors of cell death in the immune system", Annu. Rev. Immunol., 17:781-828 (1999).
Riddell, et al., "T-cell therapy of leukemia", Cancer Controll, 9:114-122 (2002).
Rocha, at al., "Peripheral selection of the T cell repertoire", Science, 251:1225-1228 (1991).
Sakaguchi, et al., "Immunologic self-tolerance maintained by activated T cells expressing IL-2 receptor alpha-chains (CD25). Breakdown of a single mechanism of self-tolerance causes various autoimmune diseases", J. Immunol., 155:1151-1164 (1995).
Savoldo, et al., "The use of cytotoxic t cells for the prevention and treatment of Epstein-Barr virus induced lymphoma in transplant recipients", Leuk. Lymphoma, 39:455-464 (2000).
Schluns and Lefrancois, "Cytokine control of memory T-cell development and survival", Nat. Rev. Immunol., 3:269-279 (2003).
Schoenberger, et al., "Efficient direct printing of tumor-specific cytotoxic T lymphocyte in vivo by an engineered APC", Cancer Res., 58:3094-3100 (1998).
Schwartz, "A cell culture model for T lymphocyte clonal anergy", Science, 248:1349-1356 (1990).
Shastri, "Needles in haystacks: identifying specific peptide antigens for T cells", Curr. Opin. Immunol., 8:271-7 (1996).
Shimizu, et al., "Induction of tumor immunity by removing CD25+CD4+ T cells: a common basis between tumor immunity and autoimmunity", J. Immunol., 163:5211-5218 (1999).
Songsivilai and Lachmann, "Bispecific antibody: a tool for diagnosis and treatment of disease", Clin. Exp. Immunol. 79:315-321 (1990).
Steenblock, et al., "A comprehensive platform for ex vivo T-cell expansion based on biodegradable polymeric artificial antigen-presenting cells", Mol. Ther., 16(4):765-72 (2008).
Steenblock, et al., "A comprehensive platform for T cell expansion based on biodegradable artificial antigen-presenting microparticulates", Mol.Ther., 30 (8):856-7 (2007).
Steenblock, et al., "Antigen presentation on artificial acellular substrates: modular systems for flexible, adaptable immunotherapy", Exp Opin Bio Ther., 9(4): 451-65 (2009).

(56) References Cited

OTHER PUBLICATIONS

Steenblock, et al., "Paracrine IL-2 delivery from biodegradable aAPCs outperforms exogenous cytokine addition during T cell stimulation", J Immunl. 30(8):861 (2007).

Stone, et al., "T-cell activation by soluble MHC oligomers can be described by a two-parameter binding model", Biophys. J., 81(5):2547-57 (2001).

Suhrbier, "Multi-epitope DNA vaccines", Immunol. Cell Biol., 75:402-408 (1997).

Sun et al., et al "Dual function of Drosophila cells as APCs for naïve CD8+T cells :implications for tumor immunotherapy", Immunity., 4:555-564 (1996).

Takahashi, et al., Immunologic self-tolerance maintained by CD25+CD4+ naturally anergic and suppressive T cells: Induction of autoimmune disease by breaking their anergic/suppressive state, Int. Immunol., 10:1969-1980 (1998).

Tham, et al., "Activation of antigen-specific T cells by artificial cell constructs having immobilized multimeric peptide-class I complexes and recombinant B7-Fc proteins", J. mmunol. Methods, 249:111-19 (2001).

Thery, et al., "Exosomes:composition, biogenesis and function", Nat Rev Immunol., 2:569-579 (2002).

Tigges et al., "Human herpes simplex virus (HSV)-specific CD8+ CTL clones recognize HSV-2-infected fibroblasts after treatment with IFN-gamma or when virion host shutoff functions are disabled", J. Immunol. 156, 3901-3910 (1996).

Townsend, et al., "Antigen recognition by class I-restricted T lymphocytes", Annu. Rev. Immunol., 7:601-624 (1989).

van de Weert, et al., "Protein instability in poly(lactic-co-glycolic acid) microparticles" , Pharm. Res., 17:1159-1167 (2000).

van Rensen, et al., "Liposomes with incorporated MHC class II/peptide complexes as antigen presenting vesicles for specific T cell activation", Pham. Res., 16:198-204 (1999).

Weiss, "Hot prospect for new gene amplifier", Science, 254:1292-1293 (1991).

Wick, et al., "Processing of bacterial antigens for peptide presentation on MHC class I molecules", Immunol. Rev., 172:153-62 (1999).

Wong, et al., "Human GM-CSF: molecular cloning of the complementary DNA and purification of the natural and recombinant proteins", Science, 228:810-815 (1985).

Yamaguchi and Anderson, "In vivo biocompatibility studies of medisorb® 65/35 D,L-lactide/glycolide copolymer microspheres", J. Controlled Release, 24:81-93 (1993).

Yee, et al., "Adoptive T cell therapy using antigen-specific CD8+T cell clones for the treatment of patients with metastatic melanoma: in vivo persistence, migration and antitumor effect of transferred T cells", PNAS, 99:16168-173 (2002).

Yewdell, et al., "Cell biology of antigen processing and presentation to major histocompatibility complex class I molecule-restricted T lymphocytes", Adv. in Immunol., 52:1-123 (1992).

COMPOSITIONS AND METHODS FOR ADOPTIVE AND ACTIVE IMMUNOTHERAPY

CROSS REFERENCE TO RELATED APPLICATIONS

This application claims priority under 35 U.S.C. 371 to PCT/US/2009/030966 filed Jan. 14, 2009, entitled "Compositions and Methods for Adoptive and Active Immunotherapy", by Tarek Fahmy and Erin Steenblock, which claims priority to and benefit of U.S. Provisional Patent Application No. 61/021,258 filed on Jan. 15, 2008, by Tarek Fahmy and Erin Steenblock, both of which are herein incorporated in their entirety by reference.

GOVERNMENT SUPPORT

This invention was made with government support under an appointment to the Department of Homeland Security (DHS) Scholarship and Fellowship Program, administered by the Oak Ridge Institute for Science and Education (ORISE) through an interagency agreement between the U.S. Department of Energy (DOE) and DHS. ORISE is managed by Oak Ridge Associated Universities (ORAU) under DOE contract number DE-AC05-06OR23100. The government has certain rights in the invention.

FIELD OF THE INVENTION

The present disclosure generally relates to the field of artificial antigen-presenting cells and methods of making and using these compositions.

BACKGROUND OF THE INVENTION

The aim of any immunotherapeutic treatment is to minimize nonspecific toxicity, thus utilizing the body's own mechanisms to target and kill abnormal cells. Immunotherapy can be used to prime and amplify antigen-specific lymphocytes either in vivo (active iummunotherapy) or ex vivo prior to their infusion (adoptive immunotherapy). Adoptive immunotherapy is a procedure whereby an individual's own lymphocytes are expanded ex vivo and re-infused back into the body. Both adoptive and active immunotherapy can be used as therapeutic strategies for the treatment of viral infection (Papadopoulos, et al., *N. Engl. J. Med*, 330(17): 1185-91 (1994); Savoldo, et al., *Leuk Lymphoma*, 39(5-6): 455-64 (2000)), autoimmune disease (Hori, et al., *Adv. Immunol.*, 81:331-71 (2003); Karim, et al., *J. Immunol.*, 172(2): 923-8 (2004)), or cancer (Dudley, et al., *Nat. Rev. Cancer*, 3(9):666-75 (2003); Riddell, et al., *Cancer Control*, 9(2):114-22 (2002); Yee, et al., *Proc. Natl. Acad. Sci. USA*., 99(25): 16168-73 (2002)).

The process of antigen-specific activation, expansion and differentiation that is essential to the establishment of immunity is determined to a large extent by the interaction between T cells and antigen-presenting cells (APCs). Efficient stimulation of antigen-specific T cells depends on the interaction of the T cell antigen receptor (TCR) with specific antigen in the form of a peptide/major histocompatibility complex (pMHC) on APCs. In addition to this recognition signal, co-stimulation through the B7 family of receptors on APCs, which engage the CD28 receptor and related receptors on T cells, is known to amplify antigen-specific T cell responses (Michel, et al., *Immunity*, 15(6):935-45 (2001)).

T cell activation and function is also influenced by cytokines, the largest class of immunoregulatory molecules. Cytokines are secreted by activated antigen presenting cells after T cell encounters and impact expansion, survival, effector function, and memory of stimulated T cells (Pardoll, *Nat. Rev. Immunol.*, 2(4):227-38 (2002); Fyfe, et al., *J. Clin. Oncol.*, 13(3):688-96 (1995); Schluns, et al., *Nat. Rev. Immunol*, 3(4):269-79 (2003)).

While natural APCs, notably dendritic cells (DCs), are the most potent in initiating immune responses, their use in ex vivo stimulation of antigen-specific immune responses in clinical settings involving adoptive immunotherapy has been limited because of issues related to the quality, expense, and time involved in their isolation and culture (Oelke, et al., *Nat. Med.*, 9(5):619-24 (2003)). Because T cell restriction necessitates the use of autologous DCs, custom isolation must be carried out for individual patient cases, limiting the generalization of this therapy. To address this issue, artificial APCs ("aAPCs") have been proposed based on cellular and acellular systems and have been tested in the expansion of a number of specific T cell populations for the treatment of a variety of disease states (Oelke, et al., *Nat. Med.*, 9(5):619-24 (2003); Kim, et al., *Nat. Biotechnol.*, 22(4):403-10 (2004)).

Cellular aAPCs have been created from human leukemia cell lines (Hirano, et al., *Clin. Cancer Res.*, 12(10):2967-75 (2006); Maus, et al., *Nat. Biotechnol.*, 20(2):143-8 (2002)), insect cells (Mitchell, et al., *J. Clin. Oncol.*, 20(4):1075-86 (2002); Jackson, et al., *Proc. Natl. Acad. Sci. U.S.A.*, 89(24): 12117-21 (1992); Sun, et al., *Immunity*, 4(6):555-64 (1996)), and mouse fibroblasts (Latouche, et al., *Nat. Biotechnol.*, 18(4):405-9 (2000); Schoenberger, et al., *Cancer Res.*, 58(14):3094-100 (1998)). Although physiological in nature, these systems require genetic modifications in order to effectively present antigens and may carry the risk for potential infection or tumorigenicity. Acellular approaches, which use micron-size latex or magnetic beads (Oelke, et al., *Nat. Med.*, 9(5):619-24 (2003); Levine, et al., *Science*, 272(5270):1939-43 (1996); Tha, et al., *J. Immunol. Methods*, 249(1-2):111-9 (2001)) or lipid-based vesicles with immobilized ligands (van Rensen, et al., *Pharm. Res*., 16(2):198-204 (1999); Prakken, et al., *Nat. Med.*, 6(12):1406-10 (2000); Thery, et al., *Nat. Rev. Immunol.*, 2(8):569-79 (2002)), are attractive because of the flexibility in tailoring the composition and density of ligand presentation. While these platforms may eliminate the risk of infection by utilizing synthetic constructs, they lack biocompatibility and present safety risks if not removed prior to re-infusion of the expanded cells into patients (Kim, et al., *Nat. Biotechnol.*, 22(4):403-10 (2004)). Also, there are currently no aAPC technologies that exist that incorporate all of the necessary signals for T cell activation in a safe, ready-to-use system that could be rapidly modified for antigen-specific T cell activation and expansion.

It is therefore an object of the invention to provide modular microparticulate aAPC compositions which provide for flexible addition and subtraction of elements.

It is another object of the invention to provide aAPCs and methods of use thereof for in vivo or ex vivo activation and expansion of lymphocytes, including T cells.

It is another object of the invention to provide compositions and methods for active and adoptive immunotherapy of cancer or an infection, such as a viral, bacterial, parasitic, protozoan or fungal infection.

It is another object of the invention to provide compositions and methods for the treatment of autoimmune disorders, graft rejection and graft-versus-host-disease.

SUMMARY OF THE INVENTION

Modular aAPCs and methods of their manufacture and use are provided. The modular design of these polymeric aAPCs, which involves flexible addition and subtraction of functional elements including antigen-specific and polymeric T cell receptor activators, co-stimulatory and adhesion molecules, and cytokines allows for exquisite control over the signals provided to T cells by natural APCs.

The modular aAPCs are constructed from polymeric nano- or microparticles. The external surface of the polymeric aAPCs are modified by conjugating to the surface of the microparticle a coupling agent. The coupling agent is preferably present in high density on the surface of the aAPC. Coupling agents preferably are molecules that match the polymer phase hydrophile-lipophile balance. The coupling agents can be fatty acids, hydrophobic or amphipathic peptides, or hydrophobic polymers. Coupling agents provide substrates that facilitate the modular assembly and disassembly of functional elements to the aAPCs. The coupling agents can be conjugated to affinity tags which allow for the modular assembly and disassembly of functional elements conjugated to complementary affinity tags.

Functional elements that can be associated with the polymeric aAPCs include antigen-specific and polyclonal T cell receptor activators, co-stimulatory molecules and adhesion molecules. Antigen-specific T cell receptor activators are antigen-presenting molecules that have determinants that match that of a selected subject. The antigen-presenting molecules can be MHC/HLA class I or class II molecules. The antigen-presenting molecules bind to antigens that can be peptides, polypeptides, proteins, polysaccharides, saccharides, lipids, nucleic acids, haptens or combinations thereof. In preferred embodiments the antigens (or antigenic fragment or epitope) are short peptides about 5-40 amino acids in length. The antigens can be viral antigens, bacterial antigens, parasite antigens, allergens or environmental antigens, tumor antigens, self antigens or autoantigens. Polyclonal T cell receptor activators include mitogenic lectins and antibodies that crosslink the T cell receptor complex.

The aAPCs also contain cytokines encapsulated in or incorporated into the polymeric microparticles. Incorporation of cytokines into the polymeric microparticles allows for paracrine release of the cytokines to T cells, thus recapitulating the interaction with natural APCs. The examples demonstrate that paracrine release of cytokines from aAPCs enhances T cell activation and proliferation with a lesser concentration of cytokine relative to exogenous administration. The examples also demonstrate that paracrine release of IL-2 from aAPCs results in the preferential expansion of CD8$^+$ T cells, as compared to CD4$^+$ T cells. As a result, the disclosed aAPCs, which release cytokines to T cells in a paracrine manner, are more effective than previous artificial APCs at expanding cytotoxic T lymphocytes.

The ability of these aAPCs to release cytokines in a controlled manner, coupled with their modular nature and ease of ligand attachment, results in an ideal, tunable APC capable of stimulating and expanding primary T cells. These aAPCs represent true "off-the-shelf" technology amenable to long-term storage and primed for immediate use.

Methods of using polymeric aAPCs in vivo for active immunotherapy, and ex vivo, for adoptive immunotherapy, are also provided. The methods can be used to prophylactically or therapeutically to activate T cells. The methods can be used in subjects infected with or exposed to infectious agents, subjects with or at risk of developing malignant tumors, and subjects with immunosuppressed conditions. The aAPCs may also be useful to induce tolerance. The aAPCs are also useful in methods for treating or preventing autoimmune diseases and disorders, allergic reactions, graft rejection and graft-versus-host disease by adoptive immunotherapy using aAPCs. In these methods, regulatory T cells (Tregs) are activated by aAPCs. When administered to the subject, Tregs actively and dominantly inhibit the activation and effector functions of autoreactive T cells. Another method provided herein includes the use of aAPCs to activate and expand cytotoxic T cells specific for IgE or CD40L antigens.

BRIEF DESCRIPTION OF THE DRAWINGS

FIG. 5A is a bar graph showing expression of CD25 on B6 T cell splenocytes activated by isotype control antibodies, soluble anti-CD3 and anti-CD28 antibodies or with aAPCs loaded with anti-CD3 and anti-CD28 antibodies with either encapsulated or exogenously added IL-2 as indicated. CD25 expression was determined by flow cytometry using anti-CD25-PE and anti-CD8 antibodies and gating for $CD8^+$ cells. Data are expressed as the mean PE fluorescence intensity.

DETAILED DESCRIPTION OF THE INVENTION

I. Definitions

Figure 1A:
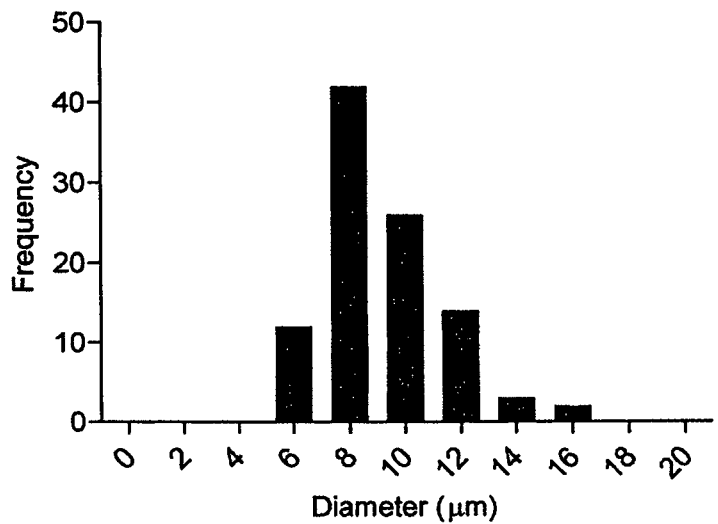
FIG. 1A is a bar graph showing size distributions for microparticles. Data are presented as the number of particles having certain diameters (μm).

Terms defined herein have meanings as commonly understood by a person of ordinary skill in the art. Terms such as "a", "an" and "the" are not intended to refer to only a singular entity, but include the general class of which a specific example may be used for illustration.

"Affinity tags" are defined herein as molecular species which form highly specific, non-covalent, physiochemical interactions with defined binding partners. Affinity tags which form highly specific, non-covalent, physiochemical interactions with one another are defined herein as "complementary".

"Coupling agents" are defined herein as molecular entities which associate with polymeric nanoparticles and provide substrates that facilitate the modular assembly and disassembly of functional elements onto the nanoparticle. Coupling agents can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Coupling agents can also be covalently coupled to functional elements in the absence of affinity tags.

An "antigen" is defined herein as a molecule which contains one or more epitopes that will stimulate a host's immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (Bergmann, et al., *Eur. J. Immunol.*, 23:2777-2781 (1993); Bergmann, et al., *J. Immunol.*, 157:3242-3249 (1996); Suhrbier, *Immunol. and Cell Biol.*, 75:402-408 (1997).

A "tumor-specific antigen" is defined herein as an antigen that is unique to tumor cells and does not occur in or on other cells in the body.

A "tumor-associated antigen" is defined herein as an antigen that is not unique to a tumor cell and is also expressed in or on a normal cell under conditions that fail to induce an immune response to the antigen.

"APCs" are defined herein as highly specialized cells that can process antigens and display their peptide fragments on the cell surface together with molecules required for lymphocyte activation. The major APCs for T cells are dendritic cells, macrophages and B cells. The major APCs for B cells are follicular dendritic cells.

As used herein the term "isolated" is meant to describe a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation).

As used herein, a "variant" polypeptide contains at least one amino acid sequence alteration (addition, deletion, substitution, preferably conservative i.e., not substantially changing the function except in magnitude) as compared to the amino acid sequence of the corresponding wild-type polypeptide.

As used herein, an "amino acid sequence alteration" can be, for example, a substitution, a deletion, or an insertion of one or more amino acids.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, a "fragment" of a polypeptide refers to any subset of the polypeptide that is a shorter polypeptide of the full length protein. Generally, fragments will be five or more amino acids in length.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

As used herein, "isolated nucleic acid" refers to a nucleic acid that is separated from other nucleic acid molecules that are present in a mammalian genome, including nucleic acids that normally flank one or both sides of the nucleic acid in a mammalian genome.

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a recombinant expression vector can be introduced.

As used herein, "transformed" and "transfected" encompass the introduction of a nucleic acid (e.g. a vector) into a cell by a number of techniques known in the art.

The terms "individual", "host", "subject", and "patient" are used interchangeably herein.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.*, 79:315-321 (1990); Kostelny et al., *J. Immunol.*, 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

As used herein, the terms "immunologic", "immunological" or "immune" response is the development of a humoral (antibody mediated) and/or a cellular (mediated by antigen-specific T cells or their secretion products) response directed against an antigen. Such a response can be an active response induced by administration of immunogen or a passive response induced by administration of antibody or primed T-cells. A cellular immune response is elicited by the presentation of polypeptide epitopes in association with Class T or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, a "costimulatory polypeptide" or a "costimulatory molecule" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory peptide.

The terms "individual", "host", "subject", and "patient" are used interchangeably herein, and refer to a mammal, including, but not limited to, murines, simians, humans, mammalian farm animals, mammalian sport animals, and mammalian pets.

II. aAPC Compositions

T cell responses are mediated by the signals received from APCs (Pardoll, *Nat. Rev. Immunol.*, 2(4):227-38 (2002)). Multivalent contacts between natural APCs and T cells are necessary to facilitate avid interactions leading to efficient stimulation of T cells (Fahmy, et al., *Immunity*, 14(2):135-43 (2001)). Efficient stimulation of antigen-specific T cells depends on the interaction of the T cell antigen receptor (TCR) with specific antigen in the form of a peptide/major histocompatibility complex (pMHC) on APCs. In addition to this recognition signal, co-stimulation through the B7 family of receptors on APCs, which engage the CD28 receptor and related receptors on T cells, is known to amplify antigen-specific T cell responses (Michel, et al., *Immunity*, 15(6):935-45 (2001)). Finally, cytokines, the largest class of immunoregulatory molecules, are secreted by activated antigen presenting cells after T cell encounters and impact expansion, survival, effector function, and memory of stimulated T cells (Pardoll, *Nat. Rev. Immunol.*, 2(4):227-38 (2002); Fyfe, et al., *J. Clin. Oncol.*, 13(3):688-96 (1995); Schluns, et al., *Nat. Rev. Immunol.*, 3(4):269-79 (2003)). No other aAPC technologies exist that incorporate all three signals in a safe, ready-to-use system that could be rapidly modified for antigen-specific T cell expansion.

Modular aAPCs are constructed from polymeric nano- or microparticles. The modular design of these polymeric aAPCs, which involves flexible addition and subtraction of functional elements including antigen-specific and polymeric T cell receptor activators, co-stimulatory and targeting molecules, and cytokines, allows for control over the signals provided to T cells by natural APCs. The ability of these aAPCs to release cytokines in a controlled manner, coupled with the ease of ligand attachment, results in an ideal, tunable aAPC capable of stimulating and expanding primary T cells. These aAPCs represent true "off-the-shelf" technology amenable to long-term storage and primed for immediate use.

A. Polymeric Micro- and Nanoparticles

As used herein, microparticles generally refers to both microparticles in the range of between 0.5 and 1000 microns and nanoparticles in the range of between 50 nm to less than 0.5 nm, preferably having a diameter that is between 1 and 20 microns or having a diameter that is between 50 and 500 nm, respectively. Microparticles and nanoparticles are also referred to more specifically. As the examples below demonstrate, it has been discovered that microparticulate aAPCs are more efficient than nanoparticulate aAPCs at stimulating T cell activation. Therefore, in a preferred embodiment, the polymeric aAPCs are microparticles.

The polymer that forms the core of the modular aAPC may be any biodegradable or non-biodegradable synthetic or natural polymer. In a preferred embodiment, the polymer is a biodegradable polymer. Polymeric systems have several features that make them ideal materials for the fabrication of a modular aAPC: 1) control over the size range of fabrication, down to 100 nm or less; 2) reproducible biodegradability without the addition of enzymes or cofactors; 3) capability for sustained release of an encapsulated, protected cytokine or chemokine over a period in the range of days to months by varying factors such as the monomer ratios or polymer size, for example, polylactic acid) (PLA) to poly(glycolic acid) (PGA) copolymer ratios, potentially abrogating the booster requirement (Gupta, et al., *Adv. Drug Deliv. Rev.*, 32(3):225-246 (1998); Kohn, et al., *J. Immunol. Methods*, 95(1):31-8 (1986); Langer, et al., *Adv. Drug Deliv. Rev.*, 28(1):97-119 (1997); Jiang, et al., *Adv. Drug Deliv. Rev.*, 57(3):391-410)), well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Examples of preferred biodegradable polymers include synthetic polymers that degrade by hydrolysis such as poly(hydroxy acids), such as polymers and copolymers of lactic acid and glycolic acid, polyanhydrides, poly(ortho)esters, polyesters, polyurethanes, poly(butic acid), poly(valeric acid), poly(caprolactone), poly(hydroxyalkanoates), and poly(lactide-co-caprolactone).

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terephthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), poly(butylmethacrylate), poly(isobutyl-methacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate). The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

The foregoing materials may be used alone, as physical mixtures (blends), or as co-polymers. In a preferred embodiment, the aAPCs are formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)).

Rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

B. Coupling Agents or Ligands

The external surface of the polymeric aAPCs may be modified by conjugating to, or incorporating into, the surface of the microparticle a coupling agent or ligand.

In a preferred embodiment, the coupling agent is present in high density on the surface of the aAPC. As used herein, "high density" refers to polymeric aAPCs having a high density of ligands or coupling agents, which is preferably in the range of 1,000 to 10,000,000, more preferably 10,000-1,000.000 ligands per square micron of microparticle surface area. This can be measured by fluorescence staining of dissolved particles and calibrating this fluorescence to a known amount of free fluorescent molecules in solution.

Coupling agents associate with the polymeric aAPCs and provide substrates that facilitate the modular assembly and disassembly of functional elements to the aAPCs. Coupling agents or ligands may associate with nanoparticles through a variety of interactions including, but not limited to, hydrophobic interactions, electrostatic interactions and covalent coupling.

In a preferred embodiment, the coupling agents are molecules that match the polymer phase hydrophile-lipophile balance. Hydrophile-lipophile balances range from 1 to 15. Molecules with a low hydrophile-lipophile balance are more lipid loving and thus tend to make a water in oil emulsion while those with a high hydrophile-lipophile balance are more hydrophilic and tend to make an oil in water emulsion. Fatty acids and lipids have a low hydrophile-lipophile balance below 10.

Any amphiphilic polymer with a hydrophile-lipophile balance in the range 1-10, more preferably between 1 and 6, most preferably between 1 and up to 5, can be used as a coupling agent. Examples of coupling agents which may associate with polymeric aAPCs via hydrophobic interactions include, but are not limited to, fatty acids, hydrophobic or amphipathic peptides or proteins, and polymers. These classes of coupling agents may also be used in any combination or ratio. In a preferred embodiment, the association of adaptor elements with nanoparticles facilitates a prolonged presentation of functional elements which can last for several weeks.

In one embodiment, coupling agents can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, His$_6$, GFP, DIG, biotin and avidin. Antibodies (both monoclonal and polyclonal and antigen-binding fragments thereof) which bind to these epitopes are well known in the art.

Affinity tags that are conjugated to coupling agents allow for highly flexible, modular assembly and disassembly of functional elements which are conjugated to affinity tags which form highly specific, noncovalent, physiochemical interactions with complementary affinity tags which are conjugated to coupling agents. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In another embodiment, coupling agents are coupled directly to functional elements in the absence of affinity tags, such as through direct covalent interactions. Coupling agents can be covalently coupled to at least one species of functional element. Coupling agents can be covalently coupled to a single species of functional element or with any combination of species of functional elements in any ratio.

In a preferred embodiment coupling agents are conjugated to at least one affinity tag that provides for assembly and disassembly of modular functional elements which are conjugated to complementary affinity tags. In a more preferred embodiment, coupling agents are fatty acids that are conjugated with at least one affinity tag. In a particularly preferred embodiment, the coupling agents are fatty acids conjugated with avidin or streptavidin. Avidin/streptavidin-conjugated fatty acids allow for the attachment of a wide variety of biotin-conjugated functional elements.

The coupling agents are preferably provided on, or in the surface of, nanoparticles at a high density. This high density of coupling agents allows for coupling of the polymeric aAPCs to a variety of species of functional elements while still allowing for the functional elements to be present in high enough numbers to be efficacious.

i. Fatty Acids

The coupling agents may include fatty acids. Fatty acids may be of any acyl chain length and may be saturated or unsaturated. In a particularly preferred embodiment, the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

ii. Hydrophobic or Amphipathic Peptides

The coupling agents may include hydrophobic or amphipathic peptides. Preferred peptides should be sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric aAPCs through the hydrophobic end of the peptide and be conjugated on the hydrophilic end to a functional group.

iii. Hydrophobic Polymers

Coupling agents may include hydrophobic polymers. Examples of hydrophobic polymers include, but are not limited to, polyanhydrides, poly(ortho)esters, and polyesters such as polycaprolactone.

C. Functional Elements to be Attached to the Surface of the Polymeric aAPCs

Functional elements which associate with the polymeric APCs through modular coupling agents function to target the APCs to T cells and to recapitulate the interactions that occur between natural APCs and T cells to elicit efficient activation and expansion of T cells. Functional elements include antigen-specific and polyclonal T cell receptor ligands, co-stimulatory molecules, and T cell targeting and adhesion molecules.

Polymeric aAPCs may be associated with a single species of functional element or may be associated with any combination of disclosed functional elements in any ratio. Functional elements are associated with aAPCs through coupling agents which directly associate with the aAPCs. Functional elements may be directly or covalently coupled to coupling agents or may bind to coupling agents through complementary affinity tags conjugated to the coupling agents and functional elements. Multiple different species of functional elements may be associated with aAPCs, for instance, by conjugating each species of functional element to a separate species of affinity tag. These functional elements may then associate with aAPCs coated with coupling agents conjugated to an appropriate ratio of complementary affinity tags. Multiple species of functional elements may also be associated with aAPCs by covalently coupling each species of functional element at a desired ratio to coupling agents.

In a preferred embodiment, functional elements are conjugated to biotin. Biotin conjugation allows the functional elements to interact with coupling agents conjugated with avidin, neutravidin or streptavidin.

i. T cell Receptor Activators a. Antigen-specific T Cell Receptor Activators

Antigen molecules are recognized by the immune system after internal processing by natural APCs (Lanzavecchia, *Curr. Opin. Immunol.*, 8:348-54 (1996)). In order to present an antigen, the antigen is broken down into small peptidic fragments by enzymes contained in vesicles in the cytoplasm of the APCs (Wick, et al., *Immunol. Rev.*, 172:153-62 (1999); Lehner, et al., *Curr. Biol.*, 8: R605-8 (1998); Braciale, *Curr. Opin. Immunol.*, 4:59-62 (1992)). The enzymes are part of a complex of proteolytic enzymes called a proteosome. Most cells have several different types of proteosomes with differing combinations of specificities, which they use to recycle their intracellular proteins. The peptides produced by the proteosomes are generated in the cytosol and transported into the Golgi, where they are linked to cellular major histocompatibility complex (MHC) molecules. These are referred to as human leukocyte antigens, or "HLAs", in human. MHC and HLA are used interchangeably herein unless specified otherwise.

ii. HLA and MHC Molecules

In one embodiment, the aAPCs described herein contain antigen-presenting molecules having determinants which match that of a selected subject or which match any known antigen-presenting molecule determinants. The antigen-presenting molecules may be MHC/HLA class I or class II molecules.

There are two types of HLA molecules used for antigen presentation, class I and class II molecules. HLA class I molecules are expressed on the surface of all cells and HLA class II are expressed on the surface of a specialized class of cells called professional APCs. HLA class II molecules bind primarily to peptides derived from proteins made outside of an APC, but can present self (endogenous) antigens. In contrast, HLA class I molecules bind to peptides derived from proteins made inside a cell, including proteins expressed by an infectious agent (e.g., such as a virus) in the cell and by a tumor cell. When the HLA class I proteins reach the surface of the cell these molecules will thus display any one of many peptides derived from the cytosolic proteins of that cell, along with normal "self" peptides being synthesized by the cell. Peptides presented in this way are recognized by T-cell receptors which engage T-lymphocytes in an immune response against the antigens to induce antigen-specific cellular immunity.

Class I transplantation antigens of the major histocompatibility complex (MHC) or HLA are cell surface glycoproteins which present antigens to cytotoxic T-cells. They are heterodimeric and composed of a polymorphic, MHC-encoded, approximately 45 kD heavy chain, which is non-covalently associated with an approximately 12 kD β-2 microglobulin (β-2m) light chain.

The extracellular portion of the MHC Class I heavy chain is divided into three domains, α-1, α-2, and α-3, each approximately 90 amino acids long and encoded on separate exons. The α-3 domain and β-2m are relatively conserved and show amino-acid sequence homology to immunoglobulin constant domains. The polymorphic α-1 and α-2 domains show no significant sequence homology to immunoglobulin constant or variable region, but do have weak sequence homology to each other. The membrane-distal polymorphic α-1 (approximately 90 amino acids) and α-2 (approximately 92 amino acids) domains each include four anti-parallel, β-pleated sheets bordered by one α-helical regions, (the first from the α-1 and the second from the α-2 domain). The α-2 domain is attached to the less-polymorphic, membrane-proximal α-3 (approximately 92 amino acids) domain which is followed by a conserved transmembrane (25 amino acids) and an intra-cytoplasmic (approximately 30 amino acids) segment. The rat, mouse, and human Class I MHC molecules are believed to have similar structural characteristics based upon known nucleotide sequences of the various MHC Class I molecules.

The classical class I gene family includes the highly polymorphic human class I molecules HLA-A, -B, and —C, and murine class I (i.e., H-2) molecules D, K, and L. A series of structural relatives (non-classical class I molecules) has been found in humans (e.g., HLA-E, -F, -G, -H, -I, and -J; and CD1) and mice (Q, T, M, and CD1) (Shawar, et al., *Annu. Rev. Immunol.*, 12:839-880 (1994)). These molecules have the typical structure of an antigen-presenting molecule, where a polymorphic heavy chain is noncovalently associated with the conserved β2-M subunit.

In the case of human class I determinants, the determinant can be a polypeptide encoded by any of the known HLA genetic loci, as well as polypeptides encoded by genetic loci not yet discovered so long as these can present antigen to a T cell in a manner effective to activate the T cell receptor. Examples of known HLA class I genetic loci include for HLA-A: A1, A2, A3, A11, A23, A24, A25, A26, A28, A29, A30, A31, A32 and Aw33; for HLA-B: B7, B13, B18, B27, B35, B37, B38, B39, Bw31, Bw42, B44, B45, B49, Bw50, B51, Bw52, Bw53, Bw54, Bw55, Bw57, Bw58, Bw60, Bw61, Bw62, Bw63, Bw64 and Bw65; for HLA-C: $Cw1^b$, Cw2, Cw3, Cw4, Cw5, Cw6, Cw7 and Cw8.

The amino acid sequences of mammalian MHC class II alpha and beta chain proteins, as well as nucleic acids encoding these proteins, are also well known in the art and available from numerous sources including GenBank. Exemplary sequences are provided in Auffray, et al., *Nature*, 308(5957): 327-333 (1984) (human HLA DQα); Larhamrnar, et al., *Proc. Natl. Acad. Sci. U.S.A.*, 80(23):7313-7317 (1983) (human LILA DQβ); Das, et al., *Proc. Natl. Acad. Sci. U.S.A.*, 80 (12): 3543-3547 (1983) (human HLA DRα); Tonnelle, et al., *EMBO J.*, 4(11):2839-2847 (1985) (human HLA DRβ); Lawrence, et al., *Nucleic Acids Res.*, 13(20):7515-7528 (1985) (human HLA DPα); and Kelly and Trowsdale, *Nucl. Acids Res.*, 13(5):1607-1621 (1985) (human HLA DPβ)

The MHC class I or class II polypeptide selected for use with the aAPCs is typically encoded by genetic loci present in the subject to be treated.

The MHC/HLA polypeptides disclosed herein include variant polypeptides. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

A variant MHC/HLA polypeptide can have any combination of amino acid substitutions, deletions or insertions. In one embodiment, variant MHC/HLA polypeptides have an integer number of amino acid alterations such that their amino acid sequence shares at least 60, 70, 80, 85, 90, 95, 97, 98, 99, 99.5 or 100% identity with an amino acid sequence of a corresponding wild type amino acid sequence. In a preferred embodiment, variant MHC/HLA polypeptides have an amino acid sequence sharing at least 60, 70, 80, 85, 90, 95, 97, 98, 99, 99.5 or 100% identity with the amino acid sequence of a corresponding wild type polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.*, 48:443-453 (1970)); 2) BLOSSUM62 comparison matrix from Hentikoff and Hentikoff (*Proc. Natl. Acad. Sci. U.S.A.*, 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in variant MHC/HLA polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, non-polar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Variant MHC/HLA polypeptides may be modified by chemical moieties that may be present in polypeptides in a normal cellular environment, for example, phosphorylation, methylation, amidation, sulfation, acylation, glycosylation, sumoylation and ubiquitylation. Variant MHC/HLA polypeptides may also be modified with a label capable of providing a detectable signal, either directly or indirectly, including, but not limited to, radioisotopes and fluorescent compounds.

Variant MHC/HLA polypeptides may also be modified by chemical moieties that are not normally added to polypeptides in a cellular environment. Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-

(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia. Polypeptides may also include one or more D-amino acids that are substituted for one or more L-amino acids.

The variant MHC/HLA polypeptides disclosed herein may also be coupled to other polypeptides to form fusion proteins. Provided are variant MHC/HLA polypeptides having a first fusion partner comprising all or a part of a MHC/HLA polypeptide fused (i) directly to a second polypeptide or, (ii) optionally, fused to a linker peptide sequence that is fused to the second polypeptide. The presence of the fusion partner can alter the solubility, affinity and/or valency of the polypeptide. MHC/HLA fusion proteins described herein include any combination of amino acid alteration (i.e. substitution, deletion or insertion), fragment, and/or modification as described above.

iii. Antigens

Antigens can be peptides, polyeptides, proteins, polysaccharides, saccharides, lipids, nucleic acids, or combinations thereof. Because CTL epitopes usually comprise 8-10 amino acid long (Townsend, et al., *Annu. Rev. Immunol.*, 7:601-624 (1989); Monaco, *Cell*, 54:777-785 (1992); Yewdell, et al., *Adv. in Immunol.*, 52:1-123 (1992)), in one embodiment, antigens are short polypeptides. Antigenic polypeptides may be about 5 to 40 amino acids, preferably 6 to 25 amino acids, more preferably 8 to 10 amino acids, in length. Examples of antigens presented in various immune responses are described in more detail below and are generally known in the art (Engelhard, *Curr. Opin. Immun.*, 6:13-23 (1994)).

Suitable antigens are known in the art and are available from commercial government and scientific sources. Criteria for identifying and selecting effective antigenic peptides (e.g., minimal peptide sequences capable of eliciting an immune response) can be found in the art. For example, Apostolopoulos, et al. (*Curr. Opin. Mol. Ther.*, 2:29-36 (2000)), discusses the strategy for identifying minimal antigenic peptide sequences based on an understanding of the three-dimensional structure of an antigen-presenting molecule and its interaction with both an antigenic peptide and T-cell receptor. Shastri, (*Curr. Opin. Immunol.*, 8:271-7 (1996)), disclose how to distinguish rare peptides that serve to activate T cells from the thousands peptides normally bound to MHC molecules.

The antigen can be derived from any source including, but not limited to, a virus, bacterium, parasite, plant, protozoan, fungus, tissue or transformed cell such as a cancer or leukemic cell. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic polypeptide. The DNA may be in the form of vector DNA such as plasmid DNA.

Antigens may be provided as single antigens or may be provided in combination. Antigens may also be provided as complex mixtures of polypeptides or nucleic acids.

a. Viral Antigens

A viral antigen can be isolated from any virus including, but not limited to, a virus from any of the following viral families: Arenaviridae, Arteriviridae, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxyiridae (e.g., vaccinia and smallpox virus), Reoviridae (e.g., rotavirus), Retroviridae (e.g., lentivirus, such as human immunodeficiency virus (HIV) I and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

b. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.* c. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Cireumsporozoite protein, a Sporozoite surface protein, a liver stage antigen, an apical membrane associated protein, or a Merozoite surface protein.

d. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including La. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia,* and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of *Hymenoptera* including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

e. Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3, 4, 5, 6, 7, GnTV, Herv-K-mel, Lage-1, Mage-A1, 2, 3, 4, 6, 10, 12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-I, GAGE-2, p15 (58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, and TPS.

f. Self Antigens or Autoantigens

The antigen may also be a self antigen or an autoantigen. Antigens may be antigens of any autoimmune or inflammatory disease or disorder including, but not limited to, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia greata, allergic responses due to arthropod bite reactions, Crohn's disease, ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis.

Preferred autoantigens of the present invention include, but are not limited to, at least a portion of a thyroid-stimulating hormone receptor, pancreatic P cell antigens, epidermal cadherin, acetyl choline receptor, platelet antigens, nucleic acids, nucleic acid protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in graft rejection include antigenic components of the graft to be transplanted into the graft recipient such as heart, lung, liver, pancreas, kidney, and neural graft components.

b. Polyclonal T Cell Receptor Activators

In another embodiment, the aAPCs described herein contain polyclonal T cell receptor activators that activate T cells in the absence of specific antigens. Suitable polyclonal T cell activators include the mitogenic lectins concanavalin-A (ConA), phytohemagglutinin (PHA) and pokeweed mitogen (PWM).

Other suitable polyclonal T cell activators include antibodies that crosslink the T cell receptor/CD3 complex. Exemplary antibodies that crosslink the T cell receptor include the HIT3a, UCHT1 and OKT3 monoclonal antibodies.

D. Co-stimulatory and T Cell Adhesion Molecules

In addition to ligation of the T cell receptor, activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)).

The polymeric aAPCs described herein contain at least one co-stimulatory molecule. Exemplary co-stimulatory molecules, also referred to as "co-stimulators", include, but are not limited to, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. Other exemplary co-stimulatory molecules that can be used include antibodies that specifically bind with a co-stimulatory molecule present on a T cell, such as, but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, and a ligand that specifically binds with CD83. Other suitable costimulatory molecules include, but are not limited to, costimulatory variants and fragments of the natural ligands described above.

Adhesion molecules may be included for the purpose of enhancing the binding association between the aAPCs and T cells. Suitable adhesion molecules include, but are not limited to, LFA-1, CD49d/29(VLA-4), CD11a/18, CD54(ICAM-1), and CD106(VCAM) and antibodies to their ligands. Other suitable adhesion molecules include antibodies to selectins L, E, and P.

E. Cytokines and Growth Factors

Cytokines, the largest class of immunoregulatory molecules, are secreted by activated APCs after T cell encounters and impact expansion, survival, effector function, and memory of stimulated T cells. Typically, cytokines are added to cultures exogenously and administered systemically to patients following re-infusion of T cells, however, such systemic administration can be associated with acute toxicity as in the case of IL-2 in clinical trials (Fyfe, et al., *J. Clin. Oncol.*, 13(3):688-96 (1995)). While exogenous addition of cytokines is a simple strategy to augment signaling, it has been discovered that paracrine release of cytokines from polymeric aAPCs represents a more efficacious strategy. The examples below demonstrate that paracrine release of cytokines from polymeric aAPCs mimics the paracrine release cytokines from natural APCs and enhances T cell activation and proliferation with a lesser concentration of cytokine relative to exogenous administration. The examples also demonstrate that paracrine release of IL-2 from aAPCs results in preferential expansion of $CD8^+$ T cells, as compared to $CD4^+$ T cells.

The aAPCs disclosed herein contain cytokines encapsulated in or incorporated into the polymeric microparticles. Suitable cytokines include, but are not limited to, hematopoietic growth factors, interleukins, interferons, immunoglobulin superfamily molecules, tumor necrosis factor family molecules and chemokines. Preferred cytokines include, but are not limited to, granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof.

Suitable chemokines include, but are not limited to, an alpha-chemokine or a beta-chemokine, including, but not limited to, a C5a, interleukin-8 (IL-8), monocyte chemotactic protein 1alpha (MIP1α), monocyte chemotactic protein 1 beta (MIP1β), monocyte chemoattractant protein 1 (MCP-1), monocyte chemoattractant protein 3 (MCP-3), platelet activating factor (PAFR), N-formyl-methionyl-leucyl-[$^3$H]phenylalanine (FMLPR), leukotriene $B_4$, gastrin releasing peptide (GRP), RANTES, eotaxin, lymphotactin, IP10, I-309, ENA78, GCP-2, NAP-2 and MGSA/gro, and variants and fragments thereof.

It is known that polypeptides can be instable during preparation, storage and release from polymeric microparticles. Cytokines that are encapsulated in or incorporated into the polymeric microparticles may be first stabilized by complexing or mixing with preservation agents. Suitable preservation agents include, but are not limited to, trehalose, mannitol, PEG 400, PEG 2000, PEG 3350, albumins, phosphatidylcholine, gelatin, tweens and pluronics.

F. Contrast Agents and other Markers

Optionally, modular polymeric aAPCs may further include agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DiD, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

Additionally radionuclides can be used as imaging agents. Suitable radionuclides include, but are not limited to radioactive species of Fe(III), Fe(II), Cu(II), Mg(II), Ca(II), and Zn(II) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

G. Pharmaceutically Acceptable Excipients

The compositions may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid fillers, dilutants or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In the preferred embodiment, administration is by injection. Typical formulations for injection include a carrier such as sterile saline or a phosphate buffered saline. Viscosity modifying agents and preservatives are also frequently added.

Optional pharmaceutically acceptable excipients especially for enteral, topical and mucosal administration, include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (POLYPLASDONE® XL from GAF Chemical Corp).

Stabilizers are used to inhibit or retard decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the particles may also contain minor amount of nontoxic auxiliary substances such as wetting or emulsifying agents, dyes, pH buffering agents, or preservatives.

The particles may be complexed with other agents. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

The particles may be further coated. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Röhm Pharma, Darmstadt, Germany), zein, shellac, and polysaccharides. Additionally, the coating material may contain conventional carriers such as plasticizers, pigments, colorants, glidants, stabilization agents, pore formers and surfactants.

III. Methods of Manufacture

A. Methods of Making Cytokine-encapsulated Microparticles

Many different processes can be used to form the nano- or microparticles. If the process does not produce particles having a homogenous size range, then the particles can be separated using standard techniques such as sieving to produce a population of particles having the desired size range.

i. Solvent Evaporation

Methods for forming nanoparticles using solvent evaporation techniques are described in E. Mathiowitz, et al., *J. Scanning Microscopy*, 4:329 (1990); Beck, et al., *Fertil. Steril.*, 31:545 (1979); Beck, et al., *Am. J. Obstet. Gynecol.*, 135(3) (1979); Benita, et al., *J. Pharm. Sci.*, 73:1721 (1984); and U.S. Pat. No. 3,960,757 to Morishita, et al. The polymer is dissolved in a volatile organic solvent, such as methylene chloride. A substance to be incorporated optionally is added to the solution, and the mixture is suspended in an aqueous solution that contains a surface active agent such as poly (vinyl alcohol). Substances which can be incorporated in the nanoparticles include, but are not limited to, cytokines, chemokines, interleukins and growth factors. The resulting emulsion is stirred until most of the organic solvent evaporated, leaving solid nano- and microparticles.

In a preferred embodiment, cytokine-loaded, spherical PLGA microparticles with a mean diameter of 1-20 μm and protein loadings of up to 40% are produced by a modified version of this technique. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

ii. Hot Melt Microencapsulation

Microparticles can be formed from polymers such as polyesters and polyanhydrides using hot melt microencapsulation methods as described in Mathiowitz, et al., *Reactive Polymers*, 6:275 (1987). In this method, the use of polymers with molecular weights between 3-75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to above the melting point of the polymer, for example, 5° C. Once the emulsion is stabilized, it is cooled until the polymer particles solidify. The resulting microparticles are washed by decanting with petroleum ether to give a free-flowing powder. Microparticles with sizes between one to 1000 microns are obtained with this method.

iii. Solvent Extraction

This technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure.

iv. Spray-Drying

Methods for forming microspheres using spray drying techniques are described in U.S. Pat. No. 6,620,617, to Mathiowitz et al. In this method, the polymer is dissolved in an organic solvent such as methylene chloride or in water. A known amount of an agent to be incorporated is suspended (insoluble agent) or co-dissolved (soluble agent) in the polymer solution. The solution or the dispersion then is spray-dried. Microspheres ranging between 0.1-10 microns are obtained.

v. Phase Inversion

Microparticles can be formed from polymers using a phase inversion method wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microparticles, wherein the polymer is either coated with the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating a cytokine or other substance.

B. Methods of Attaching Coupling Agents to Microparticles

Coupling agents may be conjugated to affinity tags prior to, or after their association with polymeric microparticles. In a preferred embodiment, the coupling agents are fatty acids and the affinity tag is avidin/streptavidin. In a more preferred embodiment, palmitic acid is conjugated to avidin. Avidin is dissolved at a concentration of 5 mg/ml in 37° C. prewarmed 2 ml solution of 2% deoxycholate in 1×PBS. To this solution, a 10 fold molar excess of NHS-Palmitic acid is added and the solution is stirred and sonicated in 37° C. water bath (Branson, 50 kHz freq.). The reaction is maintained at 37° C. for 24 hours after which excess palmitic acid is removed by dialysis against a 0.15% deoxycholate-PBS buffer prewarmed to 37° C. After three buffer changes, the avidin-palmitic acid conjugate is verified by reverse phase HPLC on a Prevail C18 column with a linear methanol gradient in 1×PBS as the mobile phase and UV detection at 280 nm. This method is easily adapted to conjugate avidin to any fatty acid of choice.

Avidin may be coupled to peptides and polymers by similar techniques. The chemistry involved in the coupling reaction will depend on the nature of available functional groups on the fatty acid, peptide or polymer. Methods for conjugating avidin to fatty acids, peptides and polymers are well known in the art. Methods for conjugating other affinity tags such as biotin, epitope tags (HA, FLAG, c-myc) and antibodies to fatty acids, peptides and polymers are well known in the art.

In a preferred embodiment, coupling agents such as those described above, including fatty acids, hydrophobic or aliphatic peptides, and polymers, are conjugated onto the surface of microparticles at the emulsion stage of microparticle preparation. In a particularly preferred embodiment, the microparticles include PLGA and the coupling agents include avidin-conjugated palmitic acid. Dissolved. PLGA solution is added to a 4 ml solution of 2 parts avidin-palmitic acid, 2 parts 5% PVA. A 50:50 mixture of protein-palmitic acid conjugates and 5% PVA has been found to yield optimal surface coverage of avidin groups on nano- and microsized particles.

C. Methods for Producing Polypeptides

Isolated polypeptides can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well know in the art include, for example, *Escherichia coli* strains such as BL-21, and cultured mammalian cells such as CHO cells.

In eukaryotic host cells, a number of viral-based expression systems can be utilized to express polypeptides. Viral based expression systems are well known in the art and include, but are not limited to, baculoviral, SV40, retroviral, or vaccinia based viral vectors.

Mammalian cell lines that stably express variant costimulatory polypeptides can be produced using expression vectors with appropriate control elements and a selectable marker. For example, the eukaryotic expression vectors pCR3.1 (Invitrogen Life Technologies) and p91023(B) (see Wong et al. (1985) *Science* 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of an expression vector by electroporation, lipofection, calcium phosphate, or calcium chloride co-precipitation, DEAE dextran, or other suitable transfection method, stable cell lines can be selected (e.g., by antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, polypeptides can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Polypeptides can be isolated using, for example, chromatographic methods such as DEAE ion exchange, gel filtration, and hydroxylapatite chromatography. For example, a polypeptide in a cell culture supernatant or a cytoplasmic extract can be isolated using a protein G column. In some embodiments, polypeptides can be "engineered" to contain an amino acid sequence that allows the polypeptides to be captured onto an affinity matrix. For example, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides.

D. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of amino acid positions that can be modified include those described herein.

E. Methods of Attaching Functional Elements to Coupling Agents

Functional elements can routinely be assembled onto coupling agents incorporated onto the microparticle surface by conjugating the functional elements to affinity tags which are complementary to the affinity tags conjugated to the coupling agents. Especially useful affinity tag pairs for use in coupling adaptor elements to functional elements are biotin-avidin and biotin-streptavidin. Affinity tag-conjugated functional elements are incubated with microparticles pre-coated with adaptor elements conjugated to complementary affinity tags under any appropriate buffer, salt and detergent conditions. For example, typical incubations may be performed at 4° C. for 2-4 hours, 37° C. for 20 minutes or room temperature for 1 hour. Incubations may be performed in phosphate buffered saline or other buffer compositions adjusted to a pH between 6.0 and 7.4. Incubation may occur with gentle shaking, rocking or rotation. Microparticles may then be washed with excess incubation buffer to remove unbound or non-specifically bound functional elements.

Functional elements may also be conjugated directly to adaptor elements in the absence of affinity tags, either prior to, or after their association with polymeric microparticles. Methods for conjugating functional elements such as peptides, polypeptides, polymers and antibodies to adaptor elements such as fatty acids, peptides and polymers are well known in the art. For example, fatty acids such as palmitic acid may be conjugated to the C-terminus of peptides, polypeptides and antibodies using a methodology similar to that described above for conjugation of palmitic acid to avidin.

IV. Methods of Use

The aAPCs are useful for activating T cells either in vivo, for active immunotherapy applications, or ex vivo, for adoptive immunotherapy applications. Activation of T cells by aAPCs increases their proliferation, cytokine production, differentiation, effector functions and/or survival. Methods for measuring these are well known to those in the art. The T cells activated by the aAPCs can be any cell which express the T cell receptor, including α/β and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In preferred embodiments the T cells that are activated are $CD8^+$ T cells. As demonstrated in the examples below, the aAPCs disclosed herein preferentially activate and expand $CD8^+$ T cells when activated ex viva or in viva, while many other aAPC platforms, both cellular and acellular, preferentially expand CD4+ T cells (Kim, et al., *Nat. Biotechnol.,* 22:403-10 (2004); Oelke, et al., *Trends Mol. Med.,* 11:412-20 (2005).

A. Subjects to be Treated

In general, the aAPCs described herein are useful for treating a subject having or being predisposed to any disease or disorder to which the subjects immune system mounts an immune response. Treating a disease or disorder to which the subject's immune system mounts an immune response may include inhibiting or delaying the development of the disease or disorder or inhibiting or reducing the symptoms of the disease or disorder. The compositions are useful as prophylactic compositions, which confer resistance in a subject to subsequent tumor development or exposure to infectious agents. The compositions are also useful as therapeutic compositions, which can be used to initiate or enhance a subject's immune response to a pre-existing antigen, such as a tumor antigen in a subject with cancer, or a viral antigen in a subject infected with a virus.

The compositions are also useful to treat or prevent diseases and disorders characterized by undesirable activation, overactivation or inappropriate activation of the immune system, such as occurs during allergic responses, autoimmune diseases and disorders, graft rejection and graft-versus-host-disease. Methods for using aAPCs for treatment of these conditions is described in more detail below.

The ability of the aAPCs to elicit T-cell mediated immune responses by activation and expansion of T cells makes these compositions especially useful for eliciting a cell-mediated response to a disease-related antigen in order to attack the disease. Thus, in a preferred embodiment, the type of disease to be treated or prevented is a malignant tumor or a chronic infectious disease caused by a bacterium, virus, protozoan, helminth, or other microbial pathogen that enters intracellularly and is attacked, i.e., by the cytotoxic T lymphocytes.

The desired outcome of a prophylactic, therapeutic or desensitized immune response may vary according to the disease, according to principles well known in the art. For example, an immune response against an infectious agent may completely prevent colonization and replication of an infectious agent, affecting "sterile immunity" and the absence of any disease symptoms. However, treatment against infectious agents with aAPCs may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

i. Subjects Infected with or Exposed to Infectious Agents

In some instances, the subject can be treated prophylactically, such as when there may be a risk of developing disease from an infectious agent. Infectious agents include bacteria, viruses and parasites. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

ii. Subjects with or a Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors. Treating a subject having a malignant tumor includes delaying or inhibiting the growth of a tumor in a subject, reducing the growth or size of the tumor, inhibiting or reducing metastasis of the tumor, and inhibiting or reducing symptoms associated with tumor development or growth. For instance, the examples below demonstrate that the aAPCs disclosed herein are effective in significantly delaying the growth of tumors in vivo.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

iii. Immunosuppressed Conditions

AAPCs can be used for treatment of disease conditions characterized by immunosuppression, including, but not limited to, AIDS or AIDS-related complex, idiopathic immunosuppression, drug induced immunosuppression, other virally or environmentally-induced conditions, and certain congenital immune deficiencies. AAPCs can also be employed to increase immune function that has been impaired by the use of radiotherapy of immunosuppressive drugs (e.g., certain chemotherapeutic agents), and therefore can be particularly useful when used in conjunction with such drugs or radiotherapy.

iv. Subjects Exposed to Allergens

The compositions and methods disclosed herein are useful to treat and/or preventing allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the disclosed vaccine compositions may lead to the production of antibodies that prevent and/or attenuate allergic reactions in subjects exposed to allergens. These can be used to enhance blocking or tolerance inducing reactions.

v. Subjects with or at Risk of Developing Autoimmune Diseases or Disorders

The compositions and methods are useful for the treatment or prevention of autoimmune diseases and disorders. Exemplary autoimmune diseases include vasculitis, Wegener's granulomatosis, Addison's disease, alopecia, ankylosing spondylitis, antiphospholipid syndrome, Behcet's disease, celiac disease, chronic fatigue syndrome, Crohn's disease, ulcerative colitis, type I diabetes, fibromyalgia, autoimmune gastritis, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vitiligo, vasculitis, small vessel vasculitis, hepatitis, primary biliary cirrhosis, rheumatoid arthritis, Chrohn's disease, ulcerative colitis, sarcoidosis, scleroderma, graft versus host disease (acute and chronic), aplastic anemia, and cyclic neutropenia.

vi. Subjects Undergoing or at Risk of Graft Rejection or Graft-versus-host Disease The compositions and methods are useful for the treatment or prevention of graft rejection or graft versus host disease. The methods and compositions can be used in the prevention or treatment of any type of allograft rejection or graft versus host disease for any type of graft, including a xenograft. The allograft can be an organ transplant, such as, but not limited to, a heart, kidney, liver, lung or pancreas. Alternatively, the allograft can be a tissue transplant, such as, but not limited to, heart valve, endothelial, cornea, eye lens or bone marrow tissue transplant. In yet other embodiments, the allograft can be a skin graft.

B. Adoptive Immunotherapy

A source of T cells is obtained from a subject to be treated for use in adoptive immunotherapy in an organism in which an immune response can be elicited, e.g., mammals. Examples of subjects include humans, dogs, cats, mice, rats, and transgenic species thereof, although humans are preferred. T cells can be obtained from a number of sources, including peripheral blood leukocytes, bone marrow, lymph node tissue, spleen tissue, and tumors. In a preferred embodiment, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through, e.g., a PERCOLL™ gradient.

A specific subpopulation of T cells, such as CD4$^+$ or CD8$^+$ T cells, can be further isolated by positive or negative selection techniques. For example, negative selection of a T cell population can be accomplished with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate CD4$^+$ cells, a monoclonal antibody cocktail typically includes antibodies to CD14, CD20, CD11b, CD16, HLA-DR, and CD8. The process of negative selection results in an essentially homogenous population of the desired T cell population.

AAPCs are customized according to the subject and the condition or disease to be treated. In one embodiment, the aAPCs contain at least one polyclonal T cell receptor activator, such as an anti-T cell receptor antibody. Polyclonal T cell activation can be useful because it can expand a T cell population more quickly than antigen-specific methods. The expanded polyclonal T cells can then be sorted to select for T cells with a specificity for the epitopes of interest. In another embodiment, the aAPCs contain MHC class I or MHC class II molecules bound to antigens of interest for antigen-specific T cell activation. The MHC polypeptides used in the aAPCs are preferably selected to match the MHC alleles expressed by the subject to be treated. The antigen is selected based on the condition or disease to be treated or prevented. The antigen may be derived from the subject to be treated.

The selected T cells are then contacted in appropriate medium with the aAPCs. AAPCs are used in amounts effective to cause activation and proliferation of T cells. The T cells are contacted with the aAPCs for periods of time necessary for expansion of the T cells. It may be advantageous to maintain long-term culture of a population of T cells following the initial activation and stimulation, by separating the T cells from the stimulus after a period of about 12 to about 14 days. In certain embodiments, it may be desirable to separate the T cells from the stimulus after a period of about 2, 3, 4, 5, 6, 7, 8, 9, 10, or 11 days. In certain embodiments, it may be desirable to separate the T cells from the stimulus after a period of less than one day, such as after about an hour, or 2, 3, 4, 5, 6, 7, 8, 9, 10, 11, 12, 13, 14, 15, 16, 17, 18, 19, 20, 21, 22, or 23 hours. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. The T cells may be stimulated through multiple rounds of activation by the aAPCs. For example, when the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells.

Following activation and expansion of the T cells, they are administered to the subject in amounts effective to induce an immune response. The T cells may be administered separately from, or in combination with, the aAPCs. The immune response induced in the animal by administering the compositions may include cellular immune responses mediated by CD8$^+$ T cells, capable of killing tumor and infected cells, and CD4$^+$ T cell responses. Humoral immune responses, mediated primarily by B cells that produce antibodies following activation by CD4$^+$ T cells, may also be induced. In a preferred embodiment, the immune response is mediated by cytolytic CD8$^+$ T cells. A variety of techniques which are well known in the art may be used for analyzing the type of immune responses induced by the compositions and methods disclosed herein (Coligan et al., *Current Protocols in Immunology*, John Wiley & Sons Inc. (1994)).

i. Adoptive Immunotherapy of Autoimmune Diseases and Disorders, Allergic Reactions, Graft Rejection and Graft-versus-host-disease Adoptive immunotherapy may also be used to treat or prevent conditions associated with undesirable activation, over-activation or inappropriate or aberrant activation of an immune response, as occurs in conditions including autoimmune disorders and diseases, allergic reactions, graft rejection and graft-versus-host disease. In one embodiment, undesirable or aberrant antigen-specific immune responses are treated or prevented by adoptive immunotherapy using "regulatory" T cells (Tregs) activated by the compositions and methods disclosed herein.

Immunological self-tolerance is critical for the prevention of autoimmunity and maintenance of immune homeostasis. The ability of the immune system to discriminate between self and non-self is controlled by mechanisms of central and peripheral tolerance. Central tolerance involves deletion of self-reactive T lymphocytes in the thymus at an early stage of development (Rocha, et al., *Science,* 251:1225-1228 (1991); Kisielow, et al., *Nature,* 333:742-746 (1988)). Several mechanisms of peripheral tolerance have been described, including T cell anergy and ignorance (Schwartz, *Science,* 248:1349-1356 (1990); Miller, et al., *Immunol. Rev.,* 133: 131-150 (1993)). Studies have provided firm evidence for the existence of a unique $CD4^+CD25^+$ population of professional regulatory/suppressor T cells that actively and dominantly prevent both the activation as well as the effector function of autoreactive T cells that have escaped other mechanisms of tolerance (Sakaguchi, et al., *J. Immunol.*, 155:1151-1164 (1995); Takahashi, et al., *Int. Immunol.*, 10:1969-1980 (1998); Itoh, et al., *J. Immunol.*, 162:5317-5326 (1999)). The elimination or inactivation of these cells resulted in severe autoimmune disease, and was also found to enhance immune responses to alloantigens and even tumors (Sakaguchi, et al., *J. Immunol.*, 155:1151-1164 (1995); Itoh, et al., *J. Immunol.*, 162:5317-5326 (1999); Shimizu, et al., *J. Immunol.*, 163: 5211-5218 (1999)). Autoantigen-specific regulatory T (Treg) cells actively regulate autoimmunity and induce long term tolerance and have application as a strategy for inducing long-lived tolerance.

T cells are obtained from the subject to be treated as described above, and a Treg enriched cell population is obtained by negative and or positive selection. An autoantigen-specific regulatory T (Treg) cell enriched composition is one in which the percentage of autoantigen-specific Treg cells is higher than the percentage of autoantigen-specific Treg cells in the originally obtained population of cells. In particular embodiments, at least 75%, 85%, 90%, 95%, or 98% of said cells of the composition are autoantigen-specific regulatory T cells. To maximize efficacy, the subpopulation is enriched to at least 90%, preferably at least 95%, and more preferably at least 98% Treg cells, preferably $CD4^+CD25^+$ $CD62L^+$ Treg cells. Positive selection may be combined with negative selection against cells comprising surface makers specific to non-Treg cell types, such as depletion of CD8, CD11b, CD16, CD19, CD36 and CD56-bearing cells.

The Treg cells are activated in a polyclonal or antigen-specific manner ex vivo using the compositions, as described above, expanded, and administered to the subject to be treated. In another embodiment, a population of T cells not enriched for Treg cells is activated and expanded, and the Treg cells are selected from the expanded T cell population using appropriate positive and/or negative selection.

Adoptive immunotherapy using Treg cells can be used for prophylactic and therapeutic applications. In prophylactic applications, Treg cells are administered in amounts effective to eliminate or reduce the risk or delay the outset of conditions associated with undesirable activation, over-activation or inappropriate or aberrant activation of an immune response, including physiological, biochemical, histologic and/or behavioral symptoms of the disorder, its complications and intermediate pathological phenotypes presenting during development of the disease or disorder. In therapeutic applications, the compositions and methods disclosed herein are administered to a patient suspected of, or already suffering from such a condition associated with undesirable activation, over-activation or inappropriate or aberrant activation of an immune response to treat, at least partially, the symptoms of the disease (physiological, biochemical, histologic and/or behavioral), including its complications and intermediate pathological phenotypes in development of the disease or disorder. An amount adequate to accomplish therapeutic or prophylactic treatment is defined as a therapeutically- or prophylactically-effective amount.

With respect to allograft rejection or graft versus host disease, in a preferred embodiment, adoptive immunotherapy with Treg cells is initiated prior to transplantation of the allograft. In certain embodiments, the Treg cells can be administered to the subject for a day, three days, a week, two weeks or a month prior to a transplantation. In other embodiments, the Treg cells are administered for a week, two weeks, three weeks, one month, two months, three months or six months following a transplantation. In a preferred embodiment, Treg cells are administered both before and after a transplantation is carried out.

The outcome of the therapeutic and prophylactic methods disclosed herein is to at least produce in a patient a healthful benefit, which includes, but is not limited to, prolonging the lifespan of a patient, delaying the onset of one or more symptoms of the disorder, and/or alleviating a symptom of the disorder after onset of a symptom of the disorder. For example, in the context of allograft rejection, the therapeutic and prophylactic methods can result in prolonging the lifespan of an allograft recipient, prolonging the duration of allograft tolerance prior to rejection, and/or alleviating a symptom associated with allograft rejection.

In another embodiment, undesirable or aberrant antigen-specific immune responses are treated or prevented by adoptive immunotherapy by using the compositions to activate and expand T cells specific for IgE or CD40L.

Immune responses to foreign, sometimes innocuous, substances such as pollen, dust mites, food antigens and bee sting can result in allergic diseases such as hay fever, asthma and systemic anaphylaxis. Immune responses to self-antigens such as pancreatic islet antigens and cartilage antigens can lead to diabetes and arthritis, respectively. The hallmark of the allergic diseases is activation of $CD4^+$ T cells and high production of IgE by B cells, whereas the salient feature of autoimmune diseases are activation of $CD4^+$ T cells and over production of inflammation cytokines. Activated $CD4^+$ T cells transiently express the self antigen CD40L.

Cytotoxic T lymphocytes (CTLs) specific for antigenic peptides derived from IgE molecule can be generated ex vivo using the artificial antigen presenting cells and methods disclosed herein presenting antigenic IgE peptides. These IgE specific CTLs can be administered to a subject to lyse the target cells loaded with IgE peptides and inhibit antigen specific IgE responses in vivo. These IgE specific CTLs can also be used to prevent or treat the development of lung inflammation and airway hypersensitivity.

Similarly, cytotoxic T lymphocytes (CTLs) specific for antigenic peptides derived from CD40L can be generated ex vivo using the artificial antigen presenting cells and methods disclosed herein presenting antigenic CD40L peptides. These CD40L specific CTLs can be administered to a subject to lyse target activated CD4$^+$ cells in vivo. These CD40L specific CTLs can be used to inhibit CD4-dependent antibody responses of all isotypes in vivo.

C. Active Immunotherapy

The aAPCs disclosed herein can also be used for active immunotherapy. For active immunotherapy, the aAPCs are administered directly to the subject to be treated in the same manner as a vaccine. In general, methods of administering polymeric microparticles and vaccines are well known in the art. Any acceptable method known to one of ordinary skill in the art may be used to administer a formulation to the subject. The administration may be localized (i.e., to a particular region, physiological system, tissue, organ, or cell type) or systemic. AAPCs can be administered by a number of routes including, but not limited to, injection: intravenous, intraperitoneal, intramuscular, or subcutaneous, to a mucosal surface (oral, sublingual or buccal, nasal, rectal, vaginal, pulmonary), or transdermal. In some embodiments, the injections can be given at multiple locations. The aAPCs can also be administered directly to an appropriate lymphoid tissue, such as the spleen, lymph nodes or mucosal-associated lymphoid tissue.

Administration of the formulations may be accomplished by any acceptable method which allows an effective amount of the aAPCs to reach their target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of aAPCs can vary according to factors including the specific antigen or combination thereof being utilized, the density and/or nature of the associated co-stimulatory molecules, the release characteristics of the encapsulated cytokines, the particular composition formulated, the mode of administration, and the age, weight, condition of the subject being treated, as well as the route of administration and the disease or disorder.

Unless defined otherwise, all technical and scientific terms used herein have the same meanings as commonly understood by one of skill in the art to which the disclosed invention belongs. Publications cited herein and the materials for which they are cited are specifically incorporated by reference.

EXAMPLES

The present invention may be further understood by reference to the following non-limiting examples.

Example 1

Fabrication of aAPCs

Materials and Methods:
Fabrication of aAPCs:
Poly(lactide-co-glycolide) (PLGA) 50/50 with an average molecular weight of 80 kDa was obtained from Durect Corporation, Cupertino, Calif. Microparticles were fabricated using a single emulsion oil-in-water technique, while nanoparticles were created using a double emulsion water-in-oil-in-water technique (Jain, *Biomaterials*, 21(23):2475-90 (2000)). Both were surface modified with avidin-palmitate conjugate as described previously (Fahmy, et al., *Biomaterials*, 26(28):5727-36 (2005)). Particles were lyophilized and stored at −20° C. until use.

Characterization of aAPCs:
Particles were imaged using scanning electron microscopy. Images were analyzed with NIH Image) to determine the size distribution of particle diameters by counting at least 150 particles per sample. For loaded IL-2 aAPCs, a controlled release profile was obtained in PBS at 37° C. ELISA analysis was performed to measure rhIL-2 levels (BD Biosciences, San Jose, Calif.).

Ligand Coupling:
Biotinylated anti-mouse CD3ε (BD Biosciences, San Jose, Calif.) or biotinylated peptide-loaded MHC-K$^b$-Ig dimers (obtained as a generous gift from Jonathan Schneck, Johns Hopkins University) (Schneck, et al., *Curr. Prot. Immunol.*, John Wiley & Sons, Inc., pp. 17.12.11-17.12.17 (2000)) and anti-mouse CD28 (BD Biosciences, San Jose, Calif.) were added at 10 µg/mL to a 10 mg/mL solution of PLGA particles in PBS and rotated at room temperature for 20 minutes. Particles were washed with PBS+1% FBS and resuspended in complete RPMI-10. Anti-CD28, when present, was added at a 1:1 molar ratio to anti-CD3 or MHC-K$^b$-Ig.

Figure 1B:
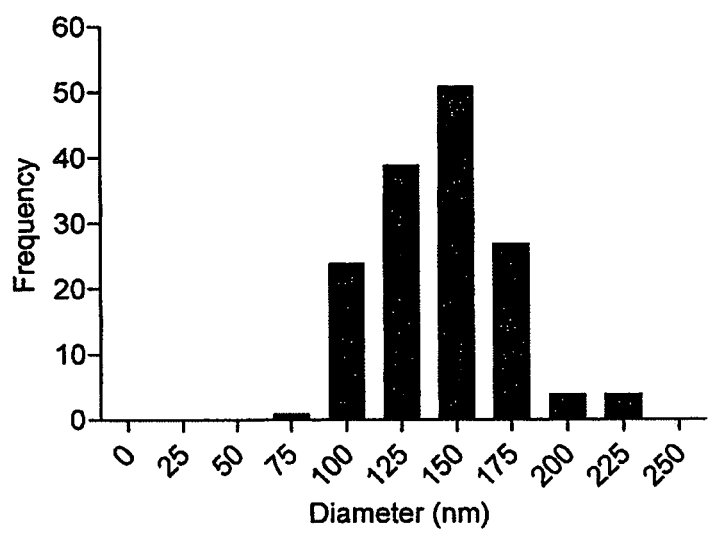
FIG. 1B is a bar graph showing size distributions for nanoparticles. Data are presented as the number of particles having certain diameters (nm).
Figure 2:
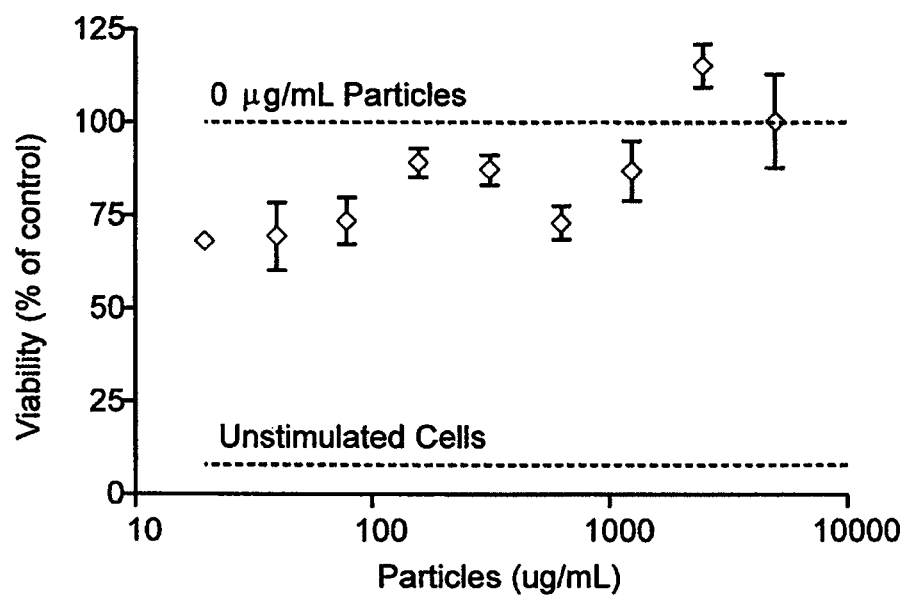
FIG. 2 is a line graph showing viability of B6 splenocytes exposed to varying concentrations of untargeted microparticles in the presence of anti-CD3 and anti-CD28 for 72 hours. Proliferation was assessed by the Cell Titer Blue Viability assay. Data are expressed as viability (percent of control) as a function of concentration of particles (μg/ml).

Results:
Both nanoparticles and microparticles were fabricated using identical formulations. Particles were created using single emulsion (microparticles) and double emulsion (micro- and nanoparticles) techniques previously described (Jain, *Biomaterials*, 21:2475-90 (2000)) and were surface modified with avidin Fahmy, et al., *Biomaterials*, 26:5727-5736 (2005)). Scanning electron microscopy revealed particles with average diameters of 8.0 µm and 130 nm for micro- and nanoparticles, respectively (FIGS. 1A and 1B). Particles were qualitatively visualized with T cells, and stable interactions were observed. The biocompatibility of untargeted aAPCs (particles without attached biotinylated ligands) was confirmed using a range of particle concentrations, and no effect on proliferation was observed (FIG. 2).

Example 2

Antigen-specific T Cell Stimulatory Effects of aAPCs

Materials and Methods:
Cell Lines and Primary Cells:
Animal studies were approved by the Institutional Animal Care and Use Committee (IACUC) at Yale University. All animals were routinely used at 6-8 weeks of age, were maintained under specific pathogen-free conditions, and were routinely checked by the Yale University Animal Resource Center. C57BL/6 (B6) mice were obtained from Jackson Laboratories (Bar Harbor, Me.). OT-I TCR transgenic breeder mice were a generous gift from Ruslan Medzhitov (Yale University) and were bred heterozygous on a B6 background in our animal facility. Phenotypes were screened using V-alpha2 and CD8a antibodies (eBioscience, San Diego, Calif.). B3Z hybridoma cells with TCR specific for SIINFEKL peptide (OVA$_{257-264}$) were a generous gift from Peter Cresswell (Yale University) and were maintained in RPMI-1640 (Invitrogen, Carlsbad, Calif.) supplemented with 10% FBS (Atlanta Biologicals, Lawrenceville, Ga.) and 2% penicillin-streptomycin (Sigma Aldrich, St. Louis, Mo.). Primary splenocytes were obtained from homogenized naive mouse spleens after depletion of erythrocytes by hypotonic lysis (Acros Organics, Geel, Belgium). Splenocytes were resuspended in complete RPMI-10, consisting of RPMI-1640 supplemented with 10% FBS, 2 mM L-glutamine (Invitrogen, Carlsbad, Calif.), 25 µM β-mercaptoethanol (American Bioanalytical, Natick, Mass.), 2% penicillin-streptomycin and 1% gentamicin (Sigma Aldrich, St. Louis, Mo.). B6 splenocytes were used without further purification, while OT-I CD8+ T cells were isolated by negative immunoselection (R&D Systems, Minneapolis, Minn.).

T Cell Stimulation Studies:

aAPCs coated with antibody or MHC were titrated across rows of a round-bottom 96-well plate (BD Biosciences, San Jose, Calif.) in 100 µl of media per well. Equal masses of micro- and nanoparticles were used, beginning with a maximum concentration of 5 mg/mL. B6 splenocytes or OT-I CD8+ T cells were added to each well at a final concentration of $5 \times 10^5$ cells/mL (B6) or $1 \times 10^5$ (OT-I). Non-biodegradable Dynal beads (4 µm diameter, Invitrogen, Carlsbad, Calif.) were used at a concentration of beads equal to the PLGA microparticle concentrations used ($1 \times 10^5$ microparticles/mg of polymer). In all cases, the highest concentration of aAPCs or beads corresponds to a 1:1 ratio of cells:particles, and the highest antibody concentration is 5 µg/mL. After incubation at 37° C. for 60 hours, plates were centrifuged at 1,500 rpm for 7 minutes in a table top centrifuge, and the supernatant was removed for IFN-γ ELISA analysis or mIL-2 ELISA. Cell pellets were resuspended in media and analyzed for viability using Cell Titer Blue (Promega, Madison, Wis.). For burst release studies, aAPCs were allowed to release IL-2 in PBS at 37° C. for 7 days prior to coupling to biotinylated anti-CD3 and anti-CD28 and use in stimulation studies. For stability studies, assembled aAPCs were incubated at 4° C. for one week before use. Reported values were obtained by using dilutions of supernatant that yielded absorbance values within the linear portion of the standard curve.

Data Fitting and Statistical Analysis:

Data fits were performed using GraphPad Prism 4.0. Controlled release data were fit to a two-phase exponential association model, and stimulation data were fit to a receptor crosslinking model (MacGlashan, et al., J. Immunol., 135: 4129-34 (1985)) where the equation of fit is given by:

$$\text{Response} = \frac{P_1 \delta}{1 + P_2 \delta} \quad \text{where} \quad \delta = \frac{C_{max} C}{(C_{max} + C)^2}$$

C is the independent variable, concentration of ligand, Cmax is the ligand concentration at which a maximal response is observed, and $P_1$ and $P_2$ are parameters relating to the height and width of the curve.

Figure 3:
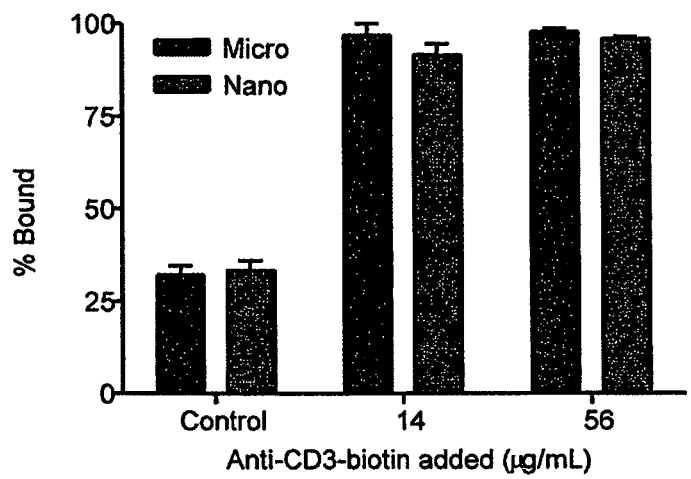
FIG. 3 is a bar graph showing binding of biotin-conjugated anti-CD3 antibody to micro- and nano-aAPCs with and without (control) avidin. aAPCs were incubated with low (14 μg/ml) and high (56 μg/ml) concentrations of anti-CD3 and bound protein content was assessed by Micro BCA Protein assay. Data are expressed as the percent of bound anti-CD3 for each condition tested.
Figure 4:
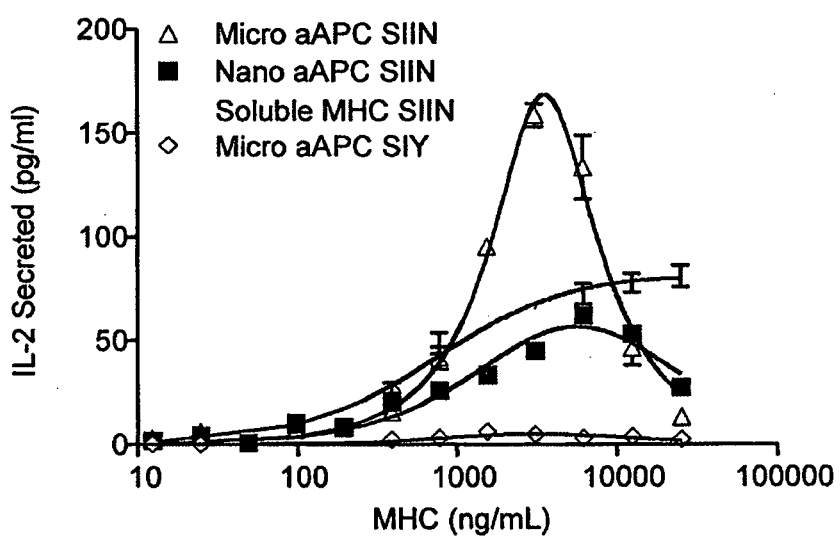
FIG. 4 is a line graph showing the secretion of IL-2 from OT-1 CD8+ T cells stimulated using micro- and nanoparticle aAPCs coupled to biotinylated MHC-K$^b$ dimers loaded with the cognate OVA SIINFEKL peptide derived from ovalbumin (OVA$_{257-264}$) ($^{SIIN}K^b$) or noncognate OVA SIYRYYGL peptide ($^{SIY}K^b$). Assembled aAPCs were serially diluted and exposed to a constant number of OT-I CD8$^+$ T cells. Activation was assessed by measuring IL-2 levels from cell culture supernatant. Data are presented for microparticle aAPCs coupled to biotinylated MHC-$^{SIIN}K^b$ (-△-) or biotinylated MHC-$^{SIY}K^b$ (-◇-), nanoparticles coupled to biotinylated MHC-$^{SIIN}K^b$ (-■-), or soluble MHC-$^{SIIN}K^b$ (-○-). Data are expressed as the concentration of secreted IL-2 (pg/ml) as a function of MHC concentration (ng/ml).

Results:

Micro- and nanoparticle aAPCs were coupled to biotinylated MHC-Kb dimers loaded with the cognate OVA SIINFEKL peptide derived from ovalbumin (OVA257-264) (Hogquist, et al., Cell, 76:17-27 (1994)) (SIINKb) or noncognate OVA SIYRYYGL peptide (SIYKb). At the concentration of ligands used in these studies (1 µg of antibody/mg polymer or 5 µg MHC/mg polymer), 90% of the protein added was successfully bound to particles (FIG. 3). To assess the optimal concentration of particles to be used with T cells, aAPCs were titrated beginning at 5 mg/mL and incubated with purified CD8+ T cells from OT-I mice, a class-I restricted T cell line recognizing the SIINFEKL peptide presented within the context of H-2 Kb. Activation was assessed by measuring IL-2 levels from cell culture supernatant. Optimal stimulation was observed to occur at an intermediate aAPC concentration, beyond which T cell IL-2 secretion declines (FIG. 4). Data were fit to a well-established model that accounts for the biophysical aspects of this trend (MacGlashan, et al., J. Immunol., 135(6):4129-34 (1985)), and model fit parameters are given in Table 1. This model predicts that activation of immune cells by multivalent ligands will exhibit bell-shaped concentration dependence due to receptor aggregation on the surface of the cells (MacGlashan, et al., J. Immunol., 135(6): 4129-34 (1985); Stone, et al., Biophys. J., 81(5):2547-57 (2001)). In this model, the decreased response at high ligand concentrations is a result of less efficient aggregation between ligands and receptors. Previous work has reported similar trends showing symmetric, bell-shaped, non-saturating concentration dependence when utilizing multivalent constructs for the stimulation of T cells (van Rensen, et al., Pharm. Res., 16(2):198-204 (1999); Stone, et al., Biophys. J., 81(5):2547-57 (2001); Fahmy, et al., Immunity, 14:135-43 (2001)).

TABLE 1

Summary of model fit parameters

| Treatment | $C_{max}$ (ng/ml) | $P_1$ | $P_2$ | R2 |
|---|---|---|---|---|
| Micorparticles | 3607.0 | 114.5 | −3.14 | 0.9646 |
| Nanoparticles | 5692.0 | 222.3 | −0.08 | 0.9126 |
| Soluble | 27574.0 | 3060.0 | 34.38 | 0.9643 |
| SIY nanocognate | 3146.0 | 17.3 | −0.75 | 0.5735 |
| aAPC anti-CD3 | 30.1 | 9.8 | −3.95 | 0.0637 |
| aAPC anti-CD3/28 | 220.5 | 2359.0 | −3.35 | 0.8909 |
| aAPC anti-CD3 | 140.8 | 3.30E+06 | 3.45 | 0.9059 |
| aAPC anti-CD3/28 | 343.4 | 1.20E+07 | −2.31 | 0.9047 |
| aAPC anti-CD3 | 97.9 | 6.2 | −3.48 | 0.4772 |
| aAPC anti-CD3/28 | 166.3 | 404.0 | −2.11 | 0.9672 |
| aAPC MHC | 3607.0 | 114.5 | −3.142 | 0.9646 |
| aAPC MHC/anti-CD28 | 3474.0 | 193.1 | −3.688 | 0.9738 |
| aAPC encapsulated IL-2 | 52.0 | 6739.0 | −2.059 | 0.9598 |
| aAPC exogenous IL-2 | 158.1 | 912.0 | −3.373 | 0.9380 |
| aAPC | 107.9 | 412.5 | −3.382 | 0.8487 |

Both micro- and nanoparticles exhibit bell-shaped curves, but the stimulation maximum for microparticle aAPCs occurs at a lower concentration of constructs than the maximal response from nanoparticle aAPCs (FIG. 4). In addition to the shift in optimal concentration, peak levels of IL-2 secretion were much higher in response to microparticle aAPCs when compared to nanoparticle aAPCs. These findings are supported by previous reports demonstrating that micron-sized particles, which are close in size to T cells, provide optimal T cell stimulation (Mescher, J. Immunol., 149(7):2402-5 (1992)). From the peak of the curve in FIG. 4, it was deduced that for this aAPC system, a ratio of 1:8, (particles:T cells) is optimal for stimulation.

Example 3

Effects of Co-stimulatory Signals on the Effectiveness of aAPCs for T Cell Stimulation Materials and Methods:

Assessment of Expansion by Flow Cytometry:

CFSE-labeled B6 splenocytes or OT-I CD8 T cells ($2\times10^6$ cells) were exposed to various concentrations of soluble ligands (anti-CD3 for polyclonal stimulation and $^{SIIN}K^b$ dimers for antigen-specific stimulation (anti-CD28 was present in both cases at a 1:1 molar ratio) or ligand coated aAPCs in the presence or absence of rhIL-2 and trehalose. Antibodies and rhIL-2 were added to achieve the indicated final concentrations in 2 mL of media. aAPCs were added at 0.3 mg/mL final concentration (40:1 cells:aAPCs). Dynal beads were used at a 3:1 ratio of beads:cells with concentrations of antibody equal to aAPCs. All antibodies, aAPCs, rhIL-2, and trehalose were added at the beginning of the experiment without restimulation during the course of the study. Cell aliquots were obtained on day 4, and flow cytometric analysis was performed using a Becton Dickenson FACScan instrument (San Jose, Calif.) and FlowJo software (Tree Star, Inc., Ashland, Oreg.). Splenocytes were stained with a 1:200 dilution of anti-CD8 PE and OT-I CD8+ T cells were stained with a 1:20 dilution of PE-labeled $^{SIIN}K^b$ tetramer (Beckman Coulter, Fullerton, Calif.). Analysis of fluorescence was performed after gating on the lymphocyte population in SSC vs. FSC plots, and, where noted, the CD8+ subset. Staining for activation markers was performed using anti-CD25, anti-CD44, and anti-CD69, all PE labeled, and subset analysis employed anti-CD4 FITC and anti-CD8 PE. All antibodies were obtained from BD Biosciences, San Jose, Calif. To measure absolute cellular expansion of splenocyte cultures, cells were analyzed on a Multisizer3 (Beckman Coulter, Fullerton, Calif.) at dilutions within the working range of the instrument. Particle counts were independently measured and subtracted from samples undergoing aAPC stimulation.

Fluorescence Microscopy:

B3Z cells were washed twice in PBS to remove serum proteins before incubation with poly-Lysine-coated cover slips (BD Biosciences, San Jose, Calif.). $1\times10^6$ cells/mL were added in serum-free RPMI 1640 at 37° C. for 1 hour. The cover slips were then blocked in RPMI-10 for 10 minutes at room temperature. aAPCs with encapsulated Rhodamine B (Acros Organics, Geel, Belgium) and attached anti-CD3 and anti-CD28 were added to cover slips at 5 mg/mL in RPMI-10. Following a 1 hour incubation at 4° C., cover slips were washed and fixed with 4% paraformaldehyde (USB Corporation, Cleveland, Ohio) for 10 minutes at room temperature. After fixing, the cells were permeabilized and stained with phalloidin-FITC (Invitrogen, Carlsbad, Calif.) and Vectashield with DAPI (Vector Laboratories, Burlingame, Calif.). Slides were visualized using a Leica SP5 confocal microscope.

Figure 5A:
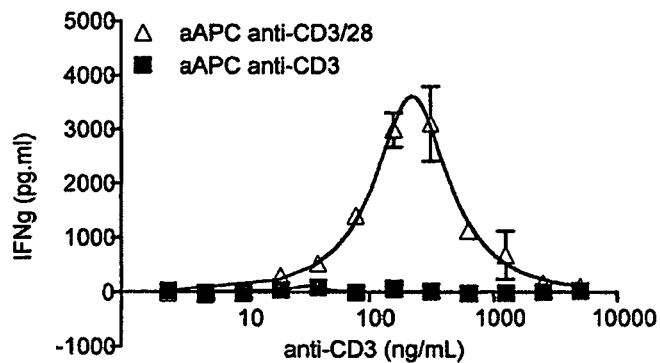
FIG. 5A is a line graph showing the secretion of INF-γ from primary B6 splenocytes stimulated using microparticle aAPCs presenting anti-CD3 alone (-■-) or anti-CD3 and anti-CD28 (-△-) in a 1:1 molar ratio. Data are expressed as the concentration of secreted INF-γ (pg/ml) as a function of anti-CD3 antibody concentration (ng/ml).
Figure 5B:
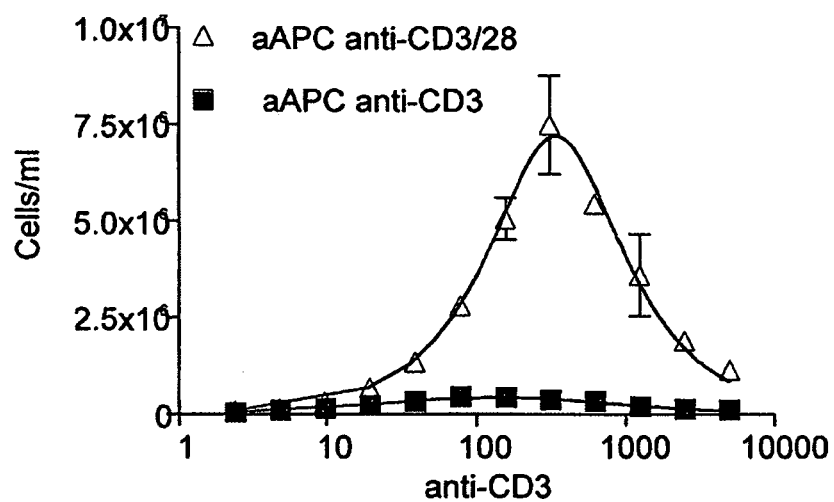
FIG. 5B is a line graph showing the proliferation of primary B6 splenocytes stimulated using microparticle aAPCs presenting anti-CD3 alone (-■-) or anti-CD3 and anti-CD28 (-△-) in a 1:1 molar ratio. Data are expressed as the number of cells per ml as a function of anti-CD3 antibody concentration (ng/ml).
Figure 5C:
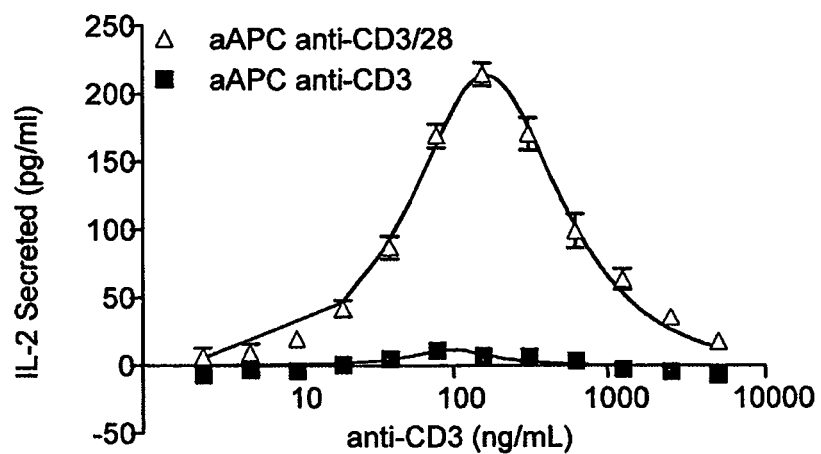
FIG. 5C is a line graph showing the secretion of IL-2 from primary B6 splenocytes stimulated using microparticle aAPCs presenting anti-CD3 alone (-■-) or anti-CD3 and anti-CD28 (-△-) in a 1:1 molar ratio. Data are expressed as the concentration of secreted IL-2 (pg/ml) as a function of anti-CD3 antibody concentration (ng/ml).
Figure 5D:
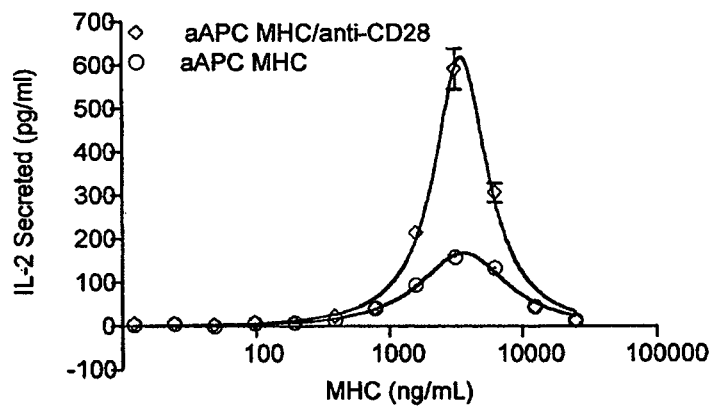
FIG. 5D is a line graph showing the secretion of IL-2 from OT-1 CD8+ T cells stimulated in an antigen-specific manner using microparticle aAPCs presenting MHC-$^{SIIN}K^b$ alone (-○-) or MHC-$^{SIIN}K^b$ and anti-CD28 (-◇-) in a 1:1 molar ratio. Data are expressed as the concentration of secreted IL-2 (pg/ml) as a function of MHC concentration (ng/ml).

Results:

aAPCs were prepared with anti-CD28 and anti-CD3 for polyclonal activation or $^{SIIN}K^b$ and anti-C28 for antigen-specific activation. IL-2 and IFN-γ secretion as well as T cell proliferation were assessed to determine activation and function of the cells. In the absence of co-stimulation, C57BL/6 (B6) T cells secreted minimal IL-2 and IFN-γ and failed to proliferate significantly (FIGS. 5A-5C). Addition of anti-CD28 induced robust cytokine secretion and enhanced proliferation. Similarly, antigen-specific stimulation was increased by a four-fold enhancement in IL-2 secretion on addition of co-stimulatory molecules to the aAPC surface (FIG. 5D). These results are consistent with previous studies that use polystyrene latex microspheres for T cell stimulation (Deeths and Mescher, *Eur. J. Immunol.*, 27:598-608 (1997)) and show that incorporation of co-stimulatory molecules on the particle surface improves T cell expansion.

Example 4

Effects of Controlled Release of IL-2 from aAPCs on T Cell Proliferation

Materials and Methods:

PLGA particles were fabricated generally as described above in Example 1. For cytokine encapsulation, 100 μg of rhIL-2 (obtained as a generous gift from Maria Parkhurst, NCI) was lyophilized with a 10-fold excess by mass of trehalose (Sigma Aldrich, St. Louis, Mo.) and incorporated as a solid during fabrication (solid-in-oil-in-water single emulsion technique) or added to 100 μl of PBS (water-in-oil-in-water emulsion technique) without trehalose.

All other materials and methods are as described above for Examples 1-3 except where indicated.

Figure 6A:
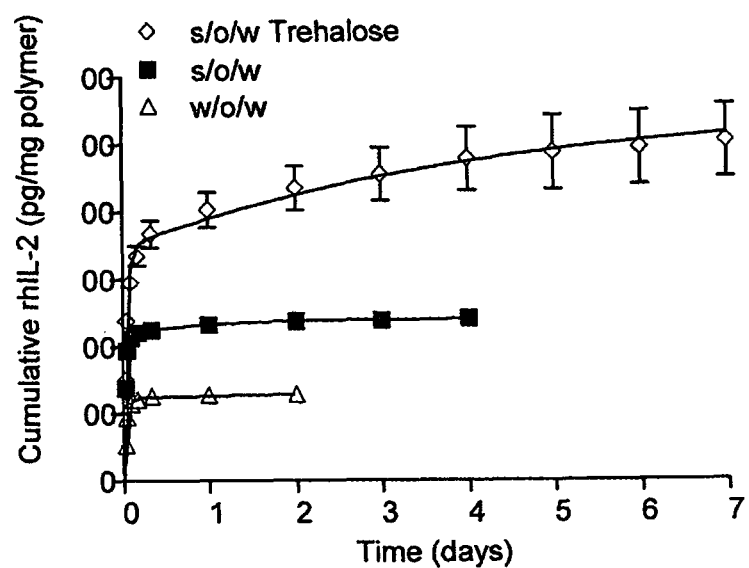
FIG. 6A is a line graph showing the kinetics of controlled release of encapsulated recombinant human IL-2 (rhIL-2) from various microparticle aAPC formulations. Microparticles were generated by double emulsion water-in-oil-in-water (w/o/w) technique (-Δ-) or by single emulsion solid-in-oil-in-water (s/o/w) technique where the rhIL-2 was either stabilized prior to encapsulation with trehalose (-◇-) or not (-■-). Data are expressed as concentration of released rhIL-2 (pg/mg polymer) as a function of time (days). The error bars represent standard deviation with n=3. Data were fit using a two-phase exponential association function.
Figure 6B:
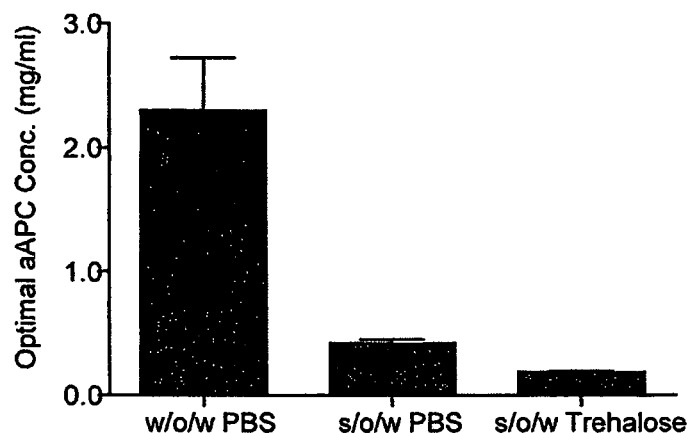
FIG. 6B is a bar graph showing the concentration of aAPCs producing peak IFN-g secretion B6 splenocytes for each of the indicated formulations. The effect of delivering rhIL-2 from microparticle aAPCs was investigated by stimulating B6 splenocytes ($5 \times 10^5$ cell/mL) far 60 hours at 37° C. aAPCs presenting anti-CD3 and anti-CD28 with varying IL-2 loads (dependent on the method of encapsulation) were titrated to determine the optimal concentration for stimulating IFN-γ production by 136 splenocytes.
Figure 6C:
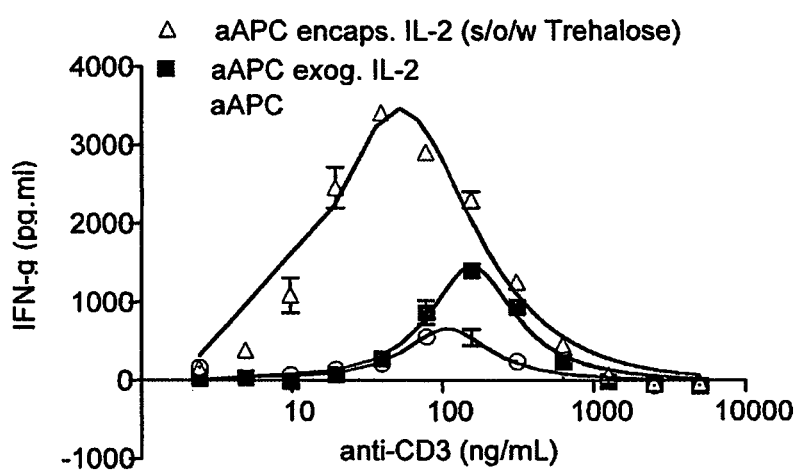
FIG. 6C is a line graph showing release of IFN-γ from B6 splenocytes stimulated by aAPCs with encapsulated IL-2 (-◇-) was compared to aAPCs with exogenous addition of the cytokine (-■-) or aAPCs without IL-2 present (-○-). Titration of all groups began at 5 mg/mL of microparticles (effective antibody concentration of 5 μg/mL). Data are expressed as the concentration of IFN-γ (pg/ml) as a function of anti-CD3 concentration (ng/ml).
Figure 6D:
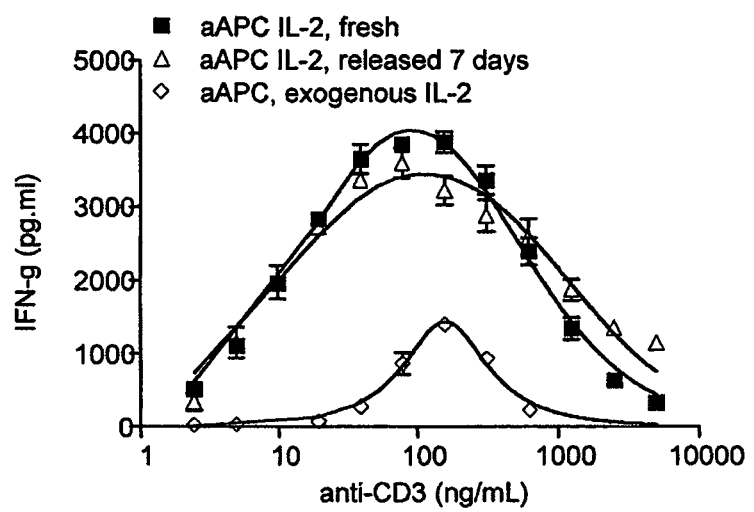
FIG. 6D is a line graph showing release of IFN-γ from 86 splenocytes stimulated by aAPCs with aAPCs with exogenous IL-2 (-◇-) or with encapsulated IL-2. Particles with encapsulated IL-2 were either applied to cells fresh (-■-) or were allowed to release IL-2 at 37° C. for 7 days, then washed before loading of antibodies and stimulation of cells (-Δ-).
Figure 6E:
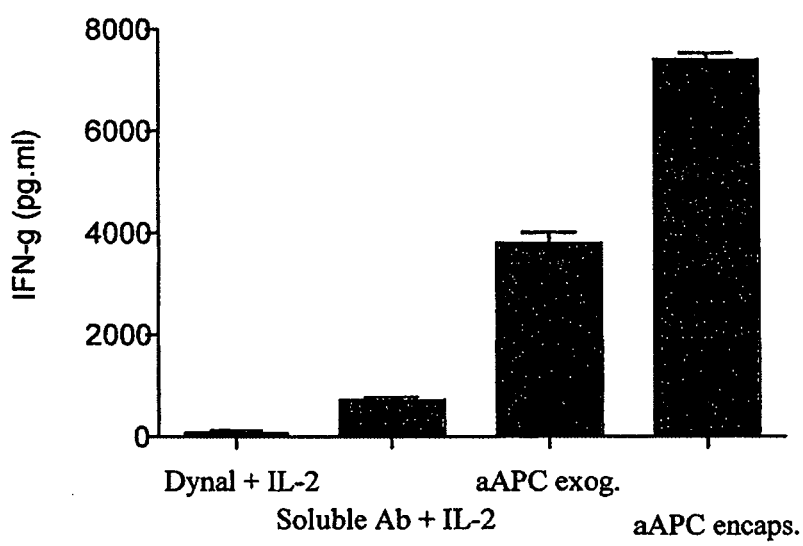
FIG. 6E is a bar graph showing release of IFN-γ from B6 splenocytes stimulated by soluble anti-CD3 and anti-CD28 antibodies, aAPCs loaded with anti-CD3 and anti-CD28 antibodies with encapsulated IL-2, aAPCs loaded with anti-CD3 and anti-CD28 antibodies plus exogenous IL-2, and Dynal magnetic beads coated with avidin plus exogenous IL-2.

Results:

The delivery of IL-2 increases the viability and proliferative capacity of T cells (Janeway et al., *Immunobiology: The Immune System in Health and Disease*, Garland Science Publishing, New York, N.Y. (2005)). A distinct advantage of the current platform is its ability to encapsulate and release, in a sustained fashion, cytokines such as IL-2. Control over release of the cytokine can be achieved by varying the particle preparation conditions. To demonstrate these features, recombinant human IL-2 (rhIL-2) was encapsulated in microparticles using three methods: 1) In phosphate buffered saline (PBS) using a double emulsion water-in-oil-in-water (w/o/w) technique (low encapsulation with burst release); 2) As a lyophilized solid using a single emulsion solid-in-oil-in-water (s/o/w) technique (medium encapsulation with burst); 3) By first stabilizing with trehalose, a known preservation agent (van de Weert, et al., *Pharmaceutical Res.*, 8:713-720 (1159-1167)), then encapsulating using a single emulsion s/o/w technique (high encapsulation and sustained release). In control experiments trehalose had neither a stimulatory nor an inhibitory effect on T cell activation. The kinetics of controlled release of rhIL-2 from each type of microparticle aAPC in PBS are shown in FIG. 6A. Controlled release curves were obtained from 10 mg of particles without attached biotinylated ligands. Attachment of surface ligands does not affect release characteristics (Fahmy, et al., *Biomaterials*, 26:5727-36 (2005)). The resulting biphasic plots are typical of protein release during PLGA particle degradation and are characterized by an initial burst release followed by continual release of protein over time (Cohen, et al., *Pharmaceutical Res.*, 8:713-20 (1991)). To examine the effect of varying rhIL-2 loading on T cell stimulation, B6 splenocytes were stimulated in a polyclonal manner by aAPCs fabricated with different rhIL-2 loading ('loaded IL-2 aAPCs') presenting anti-CD3 and anti-CD28. As expected, peak stimulation was observed with lower aAPC concentrations encapsulating higher levels of rhIL-2 that is released in a gradual manner (FIG. 6B). Furthermore, this mode of stimulation seemed to be more efficient than exogenous addition of IL-2. To show this effect, IL-2 loaded aAPCs (s/o/w trehalose-high) were compared to unloaded aAPCs in the presence and absence of equal concentrations of exogenous, titrated rhIL-2 (5 ng/mL at highest concentration). While the addition of exogenous rhIL-2 produced a moderate increase in IFN-γ secretion, paracrine delivery of rhIL-2 more than doubled this response (FIG. 6C). To determine whether this effect is due to the burst of cytokine from the particle observed at early time points or sustained release over time, particles were allowed to release rhIL-2 at 37° C. for 7 days, then washed and coupled to antibodies prior to T cell stimulation. As shown in FIG. 6D, cells exhibited only moderate decreases in IFN-γ secretion when stimulated by particles whose burst release was washed-off prior to use. This supports the hypothesis that gradual release of cytokine from the aAPC during the stimulation period has significant effects on the magnitude of stimulation. Next the performance of this system was compared to soluble antibodies and a commercially available aAPC platform, 4 μm Dynal beads (at equivalent particle concentrations) loaded with anti-CD3 and anti-CD28, in the presence of exogenous rhIL-2 (FIG. 6E). Soluble antibody and Dynal beads induced lower IFN-γ secretion than both loaded and exogenous rhIL-2 aAPCs and appear to require higher concentrations to achieve peak stimulation. Reported values for the optimal stimulation of T cells with Dynal beads suggest that a 3:1 ratio of beads to cells is ideal (Garlie, et al., *J. Immunother.*, 22:336-45 (1999)). Here, optimal stimulation with loaded IL-2 aAPCs can be achieved with a 1:64 (aAPC:T cell ratio) for polyclonal expansion (FIGS. 6C and 6D).

Example 5

Effects of Paracrine Delivery of IL-2 Versus Exogeneous IL-2 Addition on T Cell Stimulation by aAPCs Materials and Methods:

Materials and methods are generally as described above for Examples 1-4 except where indicated.

Figure 7A:
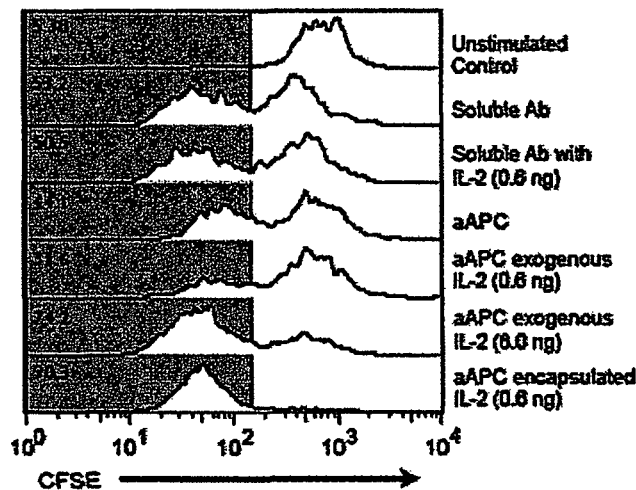
FIG. 7A is a series of histograms showing cell division of B6 T cell splenocytes stimulated with soluble anti-CD3 and anti-CD28 antibodies or with aAPCs loaded with anti-CD3 and anti-CD28 antibodies with either encapsulated or exogenously added IL-2 as indicated. Proliferation was assessed by CFSE staining. The numbers in the upper left-hand corner indicate the number of divided cells for each condition tested.
Figure 7B:
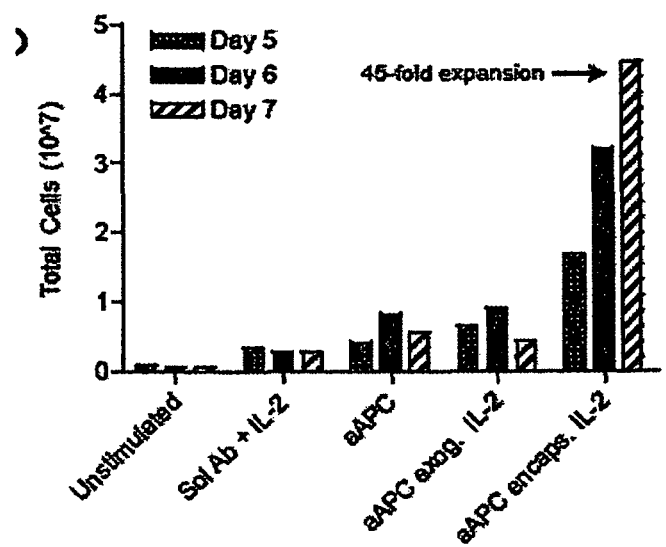
FIG. 7B is a bar graph showing proliferation of B6 T cell splenocytes at days 5, 6 and 7 following activation with the formulations specified for FIG. 7A. Data are expressed as the total number of cells ($\times 10^7$) for each formulation tested.

Results:

To examine the effect of paracrine rhIL-2 delivery on T cell expansion, CFSE dye-labeled 136 splenocytes were monitored during polyclonal stimulation. Only loaded IL-2 aAPCs produced near-complete division of T cells after 4 days of culture (FIG. 7A). Soluble antibodies and unloaded aAPCs were not as efficient in facilitating T cell division even with a 10-fold increase in the level of exogenous rhIL-2. In addition, significant improvements were observed in the absolute number of cells expanded with IL-2 loaded aAPCs. After one week of culture without restimulation, 136 splenocytes showed a 45-fold expansion in absolute cell number compared to other methods for stimulation (FIG. 7B). Polyclonal expansion of T cells led to an increase in the proportion of CD8$^+$ T cells. Addition of exogenous rhIL-2 to cultures containing unloaded aAPCs did not produce CD8$^+$ CFSE$^{LOW}$ populations equal to that of loaded IL-2 aAPCs. Increasing the concentration of exogenous rhIL-2 improved stimulation, but expansion remained less than cells treated with loaded IL-2 aAPCs. Only increasing the concentrations of soluble antibody and rhIL-2 by an order of magnitude produced comparable effects with loaded IL-2 aAPCs. Analogous results were observed with antigen-specific stimulation, where the percentage of $^{SIIN}K^b$-tetramer-positive CFSE$^{LOW}$ cells was greatest for loaded IL-2 aAPC stimulation.

Example 6 aAPCs Increase the Sensitivity of T Cells to IL-2 and Selectively Expand CD8$^+$ T Cells Materials and Methods:

Materials and methods are generally as described above for Examples 1-5 except where indicated.

Figure 8A:
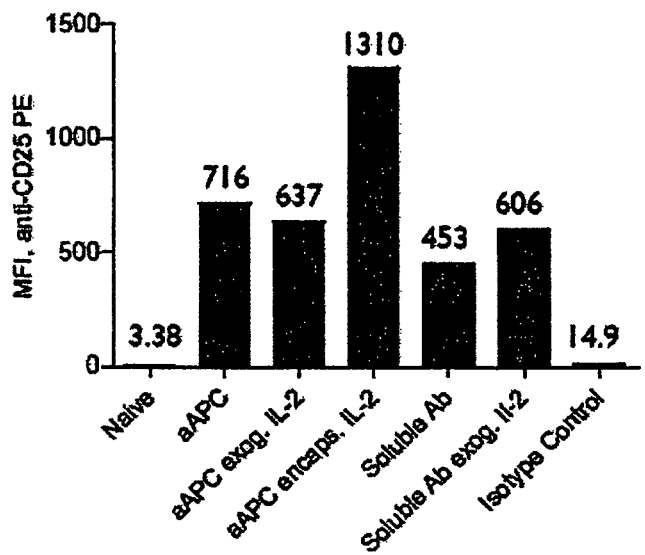
FIG. 8B is a bar graph showing the relative proportions of $CD4^+$ and $CD8^+$ T cells after stimulation of B6 T cell splenocytes activated by soluble anti-CD3 and anti-CD28 antibodies with or without exogenous IL-2, or with Dynal beads loaded with anti-CD3 and anti-CD28 antibodies with or without exogenous IL-2, or with aAPCs loaded with anti-CD3 and anti-CD28 antibodies with either encapsulated or exogenously added IL-2 as indicated.
Figure 8B:
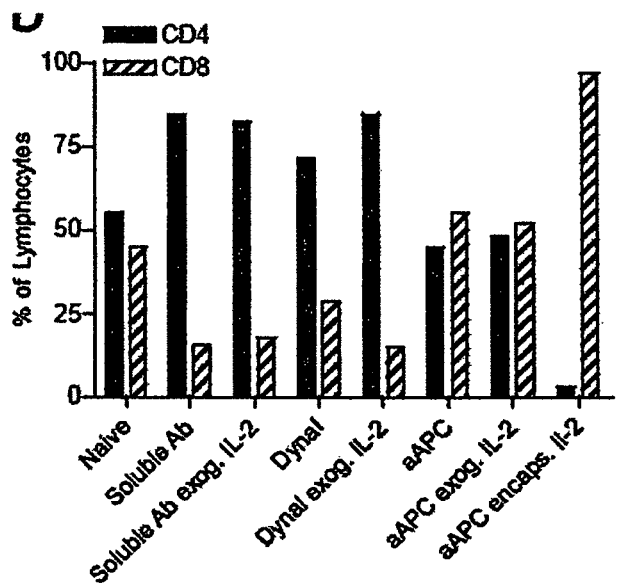
Figure 9:
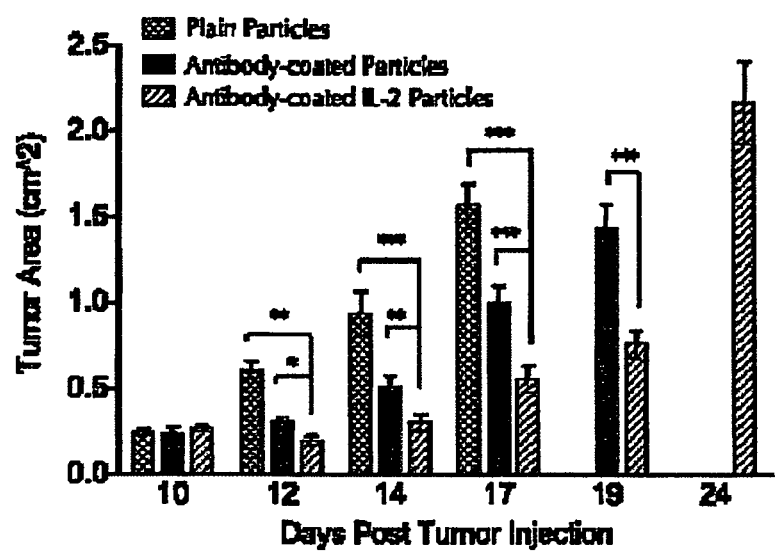
FIG. 9 is a bar graph showing the tumor area ($cm^2$) in mice as a function of days after injection with B16 melanoma tumor cells. Mice were treated either with plain particles (cross-hatched bars), particles coated with anti-CD3 and anti-CD28 antibodies (closed bars), or particles encapsulating IL-2 coated with anti-CD3 and anti-CD28 antibodies (hatched bars).

Results:

CD25, the alpha chain of the IL-2 receptor, is an established activation marker upregulated upon in vitro T cell stimulation (Gattinoni, et al., *Jour. Clin. Invest.*, 115:1616-26 (2005)). Expression of CD25 increased as a result of all stimulation methods, but was further upregulated on cells exposed to loaded IL-2 aAPCs (FIG. 5A). In addition, subset T cell analysis revealed that loaded IL-2 aAPCs preferentially expand CD8$^+$ T cells with near 100% selectivity during polyclonal expansion (FIG. 8B). This is in contrast to other methods of stimulation investigated in this work, including commercially available magnetic beads. Unloaded aAPCs with and without rhIL-2 produced near equal proportions of CD4$^+$ and CD8$^+$ T cells, while soluble antibodies and Dynal beads (used at a 3:1 ratio of beads:cells) in the presence or absence of exogenous rhIL-2 selectively expanded CD4$^+$ T cells. These results are in agreement with previous work demonstrating that some aAPC platforms, both cellular and acellular, preferentially expand CD4+ T cells (Kim, et al., *Nat. Biotechnol.*, 22:403-10 (2004); Oelke, et al., *Trends Mol. Med.*, 11:412-20 (2005)). T cells expanded with loaded IL-2 aAPCs are functional and activated as inferred from the upregulation of the activation markers CD25, CD44, and CD69.

Example 7

Induction of Effective Tumor Immunity by aAPCs in Mice

Materials and Methods:

Materials and methods are generally as described above for Examples 1-5 except where indicated.

Treatment of Mice Injected with B16 Melanoma Tumor Cells with aAPCs:

Mice were injected with B16 melanoma cells and tumors were allowed to develop. Mice were treated with aAPCs fabricated with anti-CD3 and anti-CD28 antibodies, as described above in Examples 1-3. Plain microparticles, lacking anti-CD3 and anti-CD28 antibodies were used as negative controls. Antibody-coated aAPCs were either loaded with IL-2, or were not loaded. Each mouse was injected subcutaneously on day 10 following injection of B16 melanoma cells with 2 mg of aAPCs in a total volume of 50 μl. Total tumor area of the B16 melanoma tumors was determined on days 10, 12, 14, 17, 19 and 24 following tumor cell injection.

Results:

To determine the ability of aAPCs to activate T cells in vivo, and produce effective anti-tumor immunity, a well-characterized mouse mouse cancer model, the B16 melanoma model, was used. Mice were injected with B16 melanoma tumor cells, and after allowing for the cells to develop small tumors, were injected with plain microparticles, or anti-CD3 and anti-CD28 coated microparticles, either loaded with IL-2 or left unloaded.

Administration of anti-CD3 and anti-CD28 coated microparticles (aAPCs) caused a delay in tumor development in the mice, as compared to plain microparticles, that was significantly enhanced by encapsulation of IL-2 in the aAPCs (FIG.

9). The significant delay in tumor growth was found to correlate with an expansion of cytotoxic T lymphocytes and inhibition of regulatory T cells in the vicinity of tumor growth.

We claim:

1. An artificial antigen-presenting cell (aAPC) composition comprising
polymeric nano- or microparticles,
at least one cytokine encapsulated in or incorporated into the nano- or microparticles,
coupling agents bound to or incorporated into the surface of the nano- or microparticles,
at least one T cell receptor activator bound to the nano- or microparticles, and
at least one co-stimulatory molecule bound to the nano- or microparticles,
wherein the at least one cytokine is selected from the group consisting of granulocyte macrophage colony stimulating factor (GM-CSF), tumor necrosis factor alpha (TNFα), tumor necrosis factor beta (TNFβ), macrophage colon stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof,
wherein the at least one T cell receptor activator comprises MHC molecules bound to peptide antigens, or
wherein the at least one co-stimulatory molecule is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, a ligand that specifically binds with B7-H3, a ligand that specifically binds with CD83 and antibodies that specifically bind with Toll ligand receptor, CD27, CD28, 4-1BB, OX40, CD30, CD40, PD-1, ICOS, lymphocyte function-associated antigen-1 (LFA-1), CD2, CD7, LIGHT, NKG2C and B7-H3 and variants and fragments thereof.

2. The aAPC composition of claim 1, wherein the T cell receptor activators and the co-stimulatory molecules are bound to the nano- or microparticles by the coupling agents.

3. The aAPC composition of claim 1, wherein the coupling agents are conjugated to affinity tags.

4. The aAPC composition of claim 3, wherein the coupling agents are bound to the T cell receptor activators and the co-stimulatory molecules by the non-covalent interaction of the affinity tag conjugated to the coupling agents and complementary affinity tags conjugated to the T cell receptor activators and the co-stimulatory molecules.

5. The aAPC composition of claim 1, wherein the at least one cytokine is selected from the group consisting of granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof.

6. The aAPC composition of claim 1, wherein the coupling agents are materials with a hydrophile-lipophile balance of less than 10.

7. The aAPC composition of claim 1, wherein the at least one T cell receptor activator is a polyclonal T cell receptor activator.

8. The aAPC composition of claim 1, wherein the at least one T cell receptor activator comprises MHC molecules bound to peptide antigens.

9. The aAPC composition of claim 1, wherein the at least one co-stimulatory molecule is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, a ligand that specifically binds with B7-H3, a ligand that specifically binds with CD83 and antibodies that specifically bind with Toll ligand receptor, CD27, CD28, 4-1BB, OX40, CD30, CD40, PD-1, ICOS, lymphocyte function-associated antigen-1 (LFA-1), CD2, CD7, LIGHT, NKG2C and B7-H3 and variants and fragments thereof.

10. The aAPC composition of claim 1, wherein the polymeric particles are microparticles.

11. The aAPC composition of claim 1 wherein the cytokine is IL-2, the coupling agent is biotin and the T cell activator/co-stimulatory molecule is anti-CD3.

12. A method for modulating an immune response comprising administering to an individual in need thereof or cells for administration to the individual
polymeric nano or microparticles having at least one cytokine encapsulated in or incorporated onto or into the nano- or microparticles to effect paracrine release of the cytokine,
coupling agents bound to or incorporated into the surface of the nano- or microparticles,
at least one T cell receptor activator bound to the nano- or microparticles, and
at least one co-stimulatory molecule bound to the nano- or microparticles
wherein the at least one cytokine is selected from the group consisting of granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4(IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof,
wherein the at least one T cell receptor activator comprises MHC molecules bound to peptide antigens, or
wherein the at least one co-stimulatory molecule is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, a ligand that specifically binds with B7-H3, a ligand that specifically binds with CD83 and antibodies that specifically bind with Toll ligand receptor, CD27, CD28, 4-1BB, OX40, CD30, CD40, PD-1, ICOS, lymphocyte function-associated antigen-1 (LFA-1), CD2, CD7, LIGHT, NKG2C and B7-H3 and variants and fragments thereof.

13. The method of claim 12, wherein the T cell receptor activators and/or the co-stimulatory molecules are bound to the nano- or microparticles by the coupling agents.

14. The method of claim 12, wherein the coupling agents are conjugated to affinity tags.

15. The method of claim 14, wherein the coupling agents are bound to the T cell receptor activators and the co-stimulatory molecules by the non-covalent interaction of the affinity tag conjugated to the coupling agents and complementary affinity tags conjugated to the T cell receptor activators and the co-stimulatory molecules.

16. The method of claim 12, wherein the at least one cytokine is selected from the group consisting of granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof.

17. The method of claim 12, wherein the at least one T cell receptor activator is a polyclonal T cell receptor activator.

18. The method of claim 12, wherein the at least one T cell receptor activator comprises MHC molecules bound to peptide antigens.

19. The method of claim 12, comprising at least one co-stimulatory molecule is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, a ligand that specifically binds with B7-H3, a ligand that specifically binds with CD83 and antibodies that specifically bind with Toll ligand receptor, CD27, CD28, 4-1BB, OX40, CD30, CD40, PD-1, ICOS, lymphocyte function-associated antigen-1 (LFA-1), CD2, CD7, LIGHT, NKG2C and B7-H3 and variants and fragments thereof.

20. A method for adoptive immunotherapy of a disease or disorder in an individual to be treated comprising
isolating a population of T cells from a subject to be treated,
activating the T cells by administering to the cells polymeric nano or microparticles having at least one cytokine encapsulated in or incorporated onto or into the nano- or microparticles to effect paracrine release of the cytokine,
coupling agents bound to or incorporated into the surface of the nano- or microparticles,
at least one T cell receptor activator bound to the nano- or microparticles, and
at least one co-stimulatory molecule bound to the nano- or microparticles
wherein the at least one cytokine is selected from the group consisting of granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, and variants and fragments thereof,
wherein the at least one T cell receptor activator comprises MHC molecules bound to peptide antigens, or
wherein the at least one co-stimulatory molecule is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, a ligand that specifically binds with B7-H3, a ligand that specifically binds with CD83 and antibodies that specifically bind with Toll ligand receptor, CD27, CD28, 4-1BB, OX40, CD30, CD40, PD-1, ICOS, lymphocyte function-associated antigen-1 (LFA-1), CD2, CD7, LIGHT, NKG2C and B7-H3 and variants and fragments thereof,
expanding the T cells, and
administering the T cells to the subject to be treated in an amount effective to induce an immune response.

21. The method of claim 20, wherein the aAPCs preferentially expand $CD8^+$ T cells as compared to CD4+ T cells.

22. The method of claim 12, wherein the individual to be treated has a disease or disorder selected from the group consisting of cancer, immunosuppressed conditions, or an infectious disease cause by a bacterium, virus, protozoan or helminth.

23. A method for adoptive immunotherapy of a disease or disorder characterized by over-activation, undesirable or aberrant activation of an immune response comprising
isolating a population of $CD4^+CD45^+$ T cells from a subject to be treated,
activating the $CD4^+CD45^+$T cells using the particles of claim 12,
expanding the $CD4^+CD45^+$T cells, and
administering the $CD4^+CD45^+$T cells to the subject to be treated in an amount effective to eliminate or reduce the risk or delay the outset of conditions associated with undesirable activation, over-activation or inappropriate or aberrant activation of an immune response.

24. The method of claim 12, wherein the disease or disorder is selected from the group consisting of allergic disease, autoimmune diseases or disorders, graft rejection or graft-versus-host disease.

25. The method of claim 12, wherein the disease or disorder is cancer, and wherein the amount is effective to delay or inhibit tumor growth.

26. The method of claim 12, wherein CD8+ T cells are preferentially activated, as compared to CD4+ T cells.

* * * * *